(12) United States Patent
Kimura et al.

(10) Patent No.: US 6,608,562 B1
(45) Date of Patent: Aug. 19, 2003

(54) VITAL SIGNAL DETECTING APPARATUS

(75) Inventors: Teiyuu Kimura, Nagoya (JP); Rie Ohsaki, Anjo (JP); Shinji Nanba, Kariya (JP); Satoshi Takeuchi, Nagoya (JP); Seiichi Yamada, Chirya (JP); Satoru Kodama, Obu (JP); Masao Hasegawa, Okarkai (JP); Masahiko Ito, Nagoya (JP); Tsukasa Koumura, Toyota (JP)

(73) Assignee: Denso Corporation, Kariya (JP)

( * ) Notice: Subject to any disclaimer, the term of this patent is extended or adjusted under 35 U.S.C. 154(b) by 248 days.

(21) Appl. No.: 09/651,078

(22) Filed: Aug. 30, 2000

(30) Foreign Application Priority Data

| Aug. 31, 1999 | (JP) | .......... 11-245381 |
| Sep. 1, 1999 | (JP) | .......... 11-247316 |
| Sep. 2, 1999 | (JP) | .......... 11-249025 |

(51) Int. Cl.$^7$ .............................................. G08B 23/00
(52) U.S. Cl. ................... 340/573.1; 340/539; 600/502; 600/503; 600/300; 600/344; 600/521; 128/903
(58) Field of Search .............. 340/573.1, 573.4, 340/539; 600/502, 503, 344, 300, 309, 485, 500, 508, 310, 549, 323, 521; 128/903; 988/411

(56) References Cited

U.S. PATENT DOCUMENTS

| 4,305,401 | A | * | 12/1981 | Reissmueller et al. | ....... 600/503 |
| 5,119,072 | A | * | 6/1992 | Hemingway | .............. 340/573.1 |
| 5,617,074 | A | * | 4/1997 | White | ...................... 340/573.4 |
| 5,738,104 | A | * | 4/1998 | Lo et al. | ...................... 600/521 |
| 5,766,131 | A | * | 6/1998 | Kondo et al. | ................ 600/502 |
| 5,982,285 | A | * | 11/1999 | Bueche et al. | ............ 340/573.1 |
| 6,049,282 | A | * | 4/2000 | MacKenzie | ................ 340/583 |
| 6,095,652 | A | * | 8/2000 | Trayner et al. | ............... 353/10 |
| 6,402,690 | B1 | * | 6/2002 | Rhee et al. | ................. 600/300 |

FOREIGN PATENT DOCUMENTS

| JP | 1-190332 | 7/1989 |
| JP | 5-288869 | 11/1993 |
| JP | 8-80288 | 3/1996 |
| JP | 8-266493 | 10/1996 |
| JP | 9-37056 | 2/1997 |
| JP | 9-122090 | 5/1997 |

OTHER PUBLICATIONS

Yamashita et al., "Development of a Ring–Type Vital Sign Telemeter," *Technical Report of IEICE*, vol. MBE95–40, Jun. 1995, pp. 63–68.

* cited by examiner

Primary Examiner—Benjamin C. Lee
(74) Attorney, Agent, or Firm—Posz & Bethards, PLC

(57) ABSTRACT

A vital signal detecting apparatus comprises an attachable device to be attached to a finger, a sensor having a light-emitting device and a light-receiving device, and a transmitting circuit for transmitting a signal waveform as a pulse wave from the sensor to a pulse wave monitoring unit. The pulse wave detecting unit also has an attachment detecting circuit for detecting whether or not the attachable device is in an attached state by comparing a signal waveform obtained when the light-emitting device is on with a signal waveform obtained when the light-emitting device is off and an operation control circuit for controlling the operation of the sensor, the transmitting circuit and the attachment detecting circuit. Preferably, the light-transmitting plate is disposed above the light-emitting device and the light-receiving device to pass light therethrough, and the light transmitting plate may be an IR-cut filter capable of blocking light of wavelengths greater than 700 nm.

13 Claims, 22 Drawing Sheets

FIG. 3A1
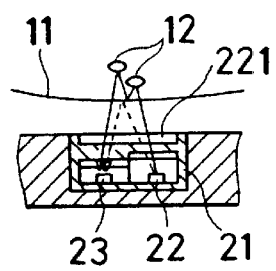
FIG. 3A2
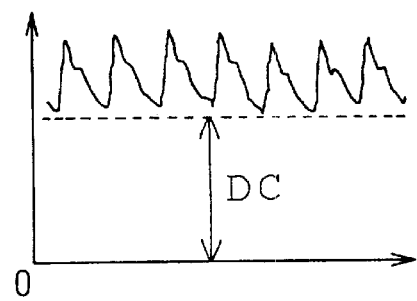
FIG. 3B1
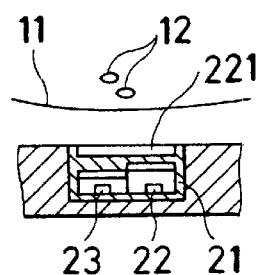
FIG. 3B2
FIG. 3C1
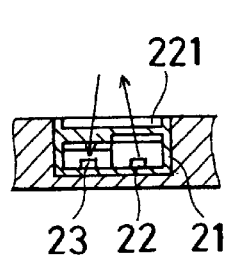
FIG. 3C2
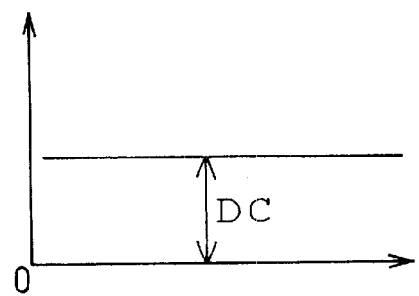
FIG. 3D1
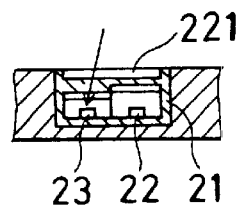
FIG. 3D2
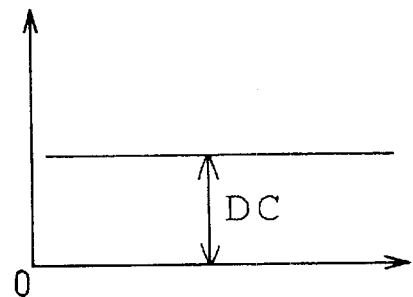

|  | DISPLAYED WAVEFORM | DISPLAY 83 |
|---|---|---|
| [1] | ——— | FINGER NOT INSERTED |
| [2] | ⋀⋀⋀ | NORMAL |
| [3] | (noisy waveform) | NOISE INGRESS |
| [4] | (fast waveform) / (slow waveform) | FAST BEATS, MISSING BEATS |

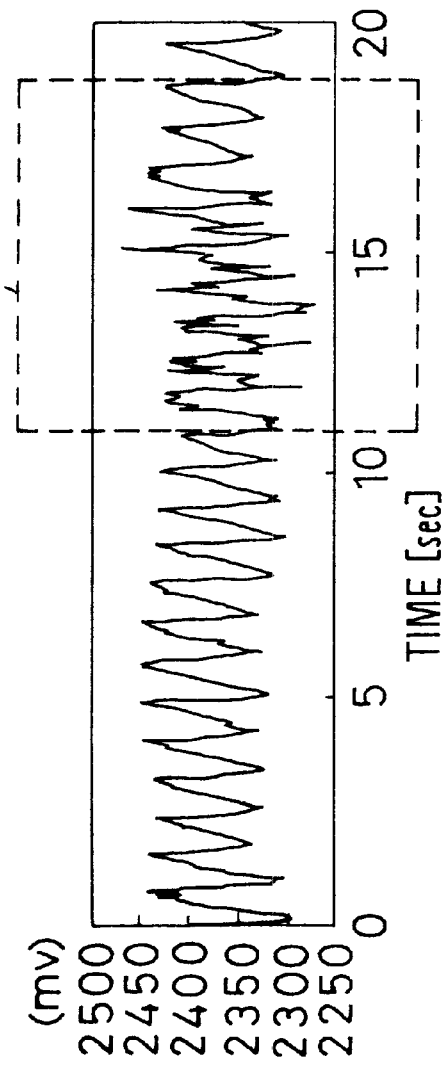 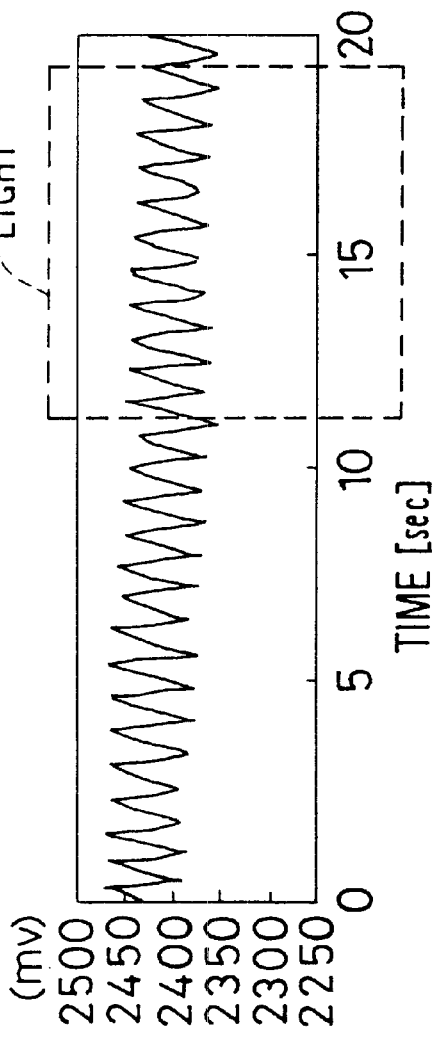
FIG. 23A
FIG. 23B

VITAL SIGNAL DETECTING APPARATUS

CROSS REFERENCE TO RELATED APPLICATION

This patent application relates to and incorporation herein by reference Japanese Patent Applications No. 11-245381 filed on Aug. 31, 1999, No. 11-247316 filed on Sep. 1, 1999 and No. 11-249025 filed on Sep. 2, 1999.

BACKGROUND OF THE INVENTION

This invention relates to a vital signal detecting apparatus for detecting a vital signal, having an attachable device to be attached for example to a finger, an ear, an arm, a leg, torso or a neck of a human subject.

There have been vital signal detecting apparatuses, as disclosed, for instance, in JP-A-8-266493 or Electronic Data Communications Society, Technical Report 1995-06. To check a vital signal (such as a pulse wave), a human subject has to operate an on/off switch himself or herself. If the subject operates the on/off switch without inserting a finger into the attachable device, because a sensor picks up external noise and outputs an abnormal signal, the vital signal checking device erroneously determines that the subject is abnormal. Further, if a ring part of a pulse wave sensor fails even slightly to match the size (thickness) of the finger, it is difficult for a detecting part to be kept in contact with the surface of the finger. Thus, extraneous light, for example, sunlight or light from fluorescent lights, affect the measurement.

There have also been vital signal detecting apparatuses, used when a vital signal (such as the pulse wave) of for example an elderly or infirm subject is to be monitored over a long period, with which an attachable device is attached for instance to an arm or a leg of the subject and a vital signal detected by a sensor is transmitted to a vital signal checking device by radio waves or the like. If the elderly or infirm subject removes the attachable device, because the sensor picks up external noise and transmits an abnormal signal to the vital signal checking device, again the vital signal checking device erroneously determines that the subject is abnormal.

SUMMARY OF THE INVENTION

It is therefore an object of the present invention to provide a vital signal detecting apparatus which eliminates problems caused by abnormal vital signals detected when an attachable device is not attached.

According to the present invention, a vital signal detecting apparatus comprises an attachable device to be attached to a finger, a sensor having a light-emitting device and a light-receiving device, and a transmitting circuit for transmitting a signal waveform as a pulse wave from the sensor to a pulse wave monitoring unit.

Preferably, the vital signal detecting unit also has an attachment detecting circuit for detecting whether or not the attachable device is in an attached state by comparing a signal waveform obtained when the light-emitting device is on with a signal waveform obtained when the light-emitting device is off and an operation control circuit for controlling the operation of the sensor, the transmitting circuit and the attachment detecting circuit.

Preferably, the light-transmitting plate is disposed above the light-emitting device and the light-receiving device to pass light therethrough, and the light transmitting plate may be an IR-cut filter capable of blocking light of wavelengths greater than 700 nm.

BRIEF DESCRIPTION OF THE DRAWINGS

The above and other objects, features and advantages of the present invention will become more apparent from the following detailed description made with reference to the accompanying drawings. In the drawings:

FIGS. 3A1 through 3D2 are views illustrating differences between signal waveforms obtained with a light-emitting diode ON (FIGS. 3A1 and 3A2, and 3C1 and 3C2) and OFF (FIGS. 3B1 and 3B2, and 3D1 and 3D2) with the attachable device fitted (FIGS. 3A1 and 3A2, and 3B1 and 3B2) and not fitted (FIGS. 3C1 and 3C2, and 3D1 and 3D2) on a finger;

FIGS. 23A and 23B are graphs showing the influence of windows of different widths on extraneous light;

Figure 1A:
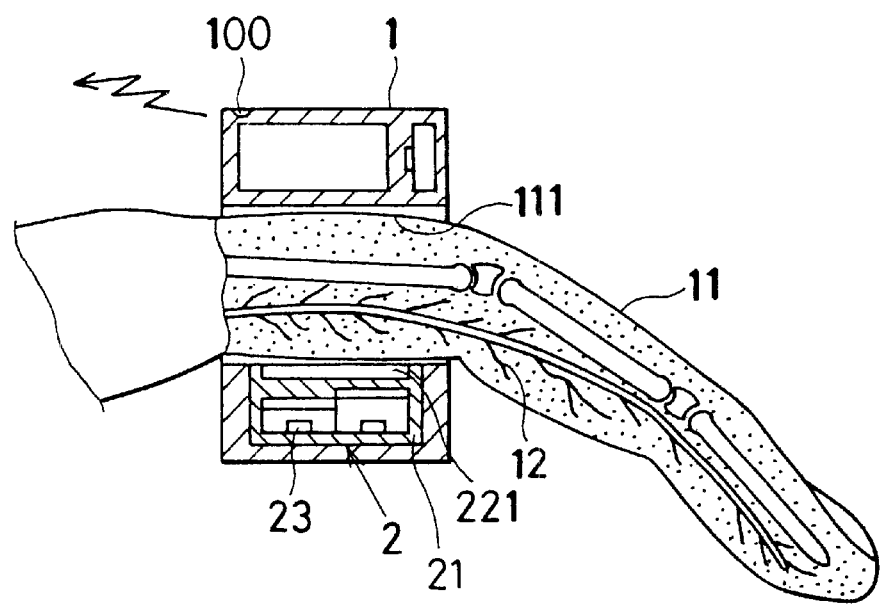
FIGS. 1A and 1B are views showing an attachable device of a pulse wave monitoring system of a first preferred embodiment of the invention.
Figure 1B:
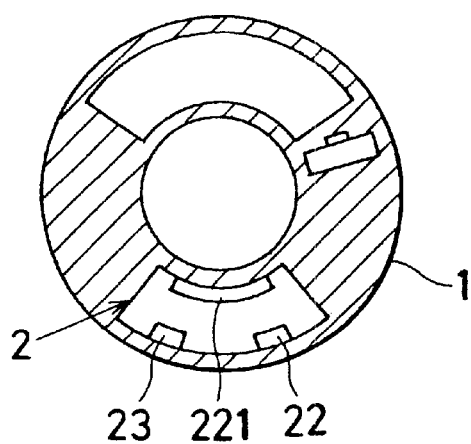

DETAILED DESCRIPTION OF THE PREFERRED EMBODIMENTS (First Preferred Embodiment)

A first preferred embodiment of the invention will now be described on the basis of FIGS. 1A and 1B through 4.

As shown in these figures, a pulse wave monitoring system K is made up of a pulse wave detecting unit A, having an attachable device 1, a vital signal detecting sensor 2, an attachment detecting circuit (ADC) 3, an operation control circuit 4, an amplifier circuit 5, a transmitting circuit (TR) 6 and a timer circuit 7, and a pulse wave monitoring unit B for monitoring a pulse wave.

The attachable device 1, which is made of plastic, is a cylinder shaped like a ring to be worn on a finger, and has an internal diameter such that a base part 111 of a finger 11 of a subject will fit in its easily and without readily slipping out (FIG. 1). A surface treatment (such as painting black) for preventing the reflection of light has been carried out on the inside of this attachable device 1. The sensor 2 has a light-emitting diode 22 and a photo diode 23 mounted in a package 21 molded inside the attachable device 1. The package 21 is made of black plastic and has a light-transmitting window 221 extending in the finger length direction. Light emitted by the light-emitting diode 22 passes through the skin of the finger 11 into the finger and reaches blood capillaries and is partly absorbed and partly scattered by reflection and returned from inside the finger, and the photo diode 23 is disposed in a position where it can receive this returning light.

The attachment detecting circuit 3 is a circuit for determining whether the attachable device 1 is fitted on the finger 11. This attachment detecting circuit 3 determines whether the attachable device 1 is fitted on the finger 11 by comparing a signal waveform obtained from the photo diode 23 when the light-emitting diode 22 is on with a signal waveform obtained when the light-emitting diode 22 is off.

Figure 2:
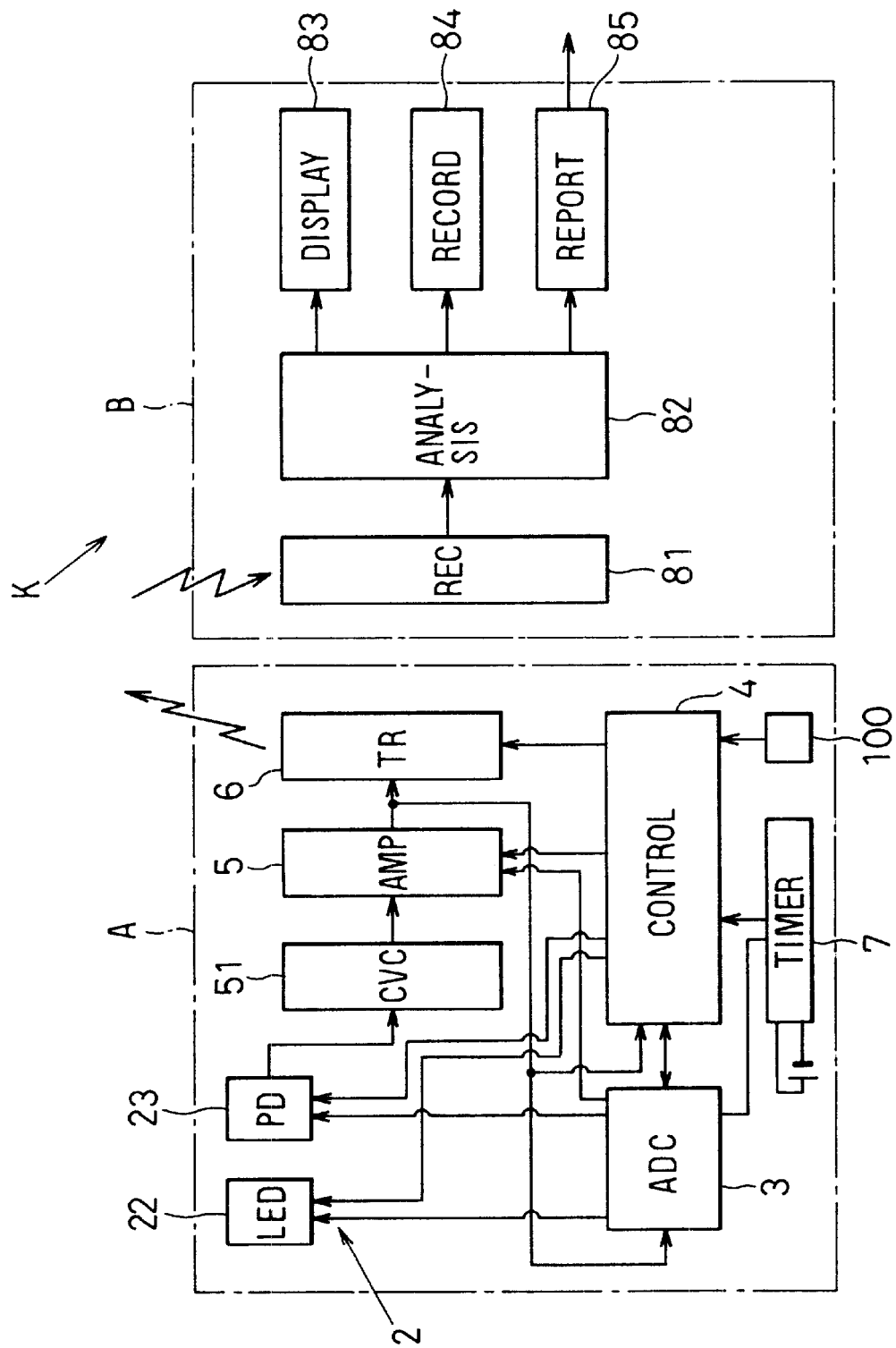
FIG. 2 is a block diagram of the pulse wave monitoring system of the first preferred embodiment.

As shown in FIGS. 3A1 through 3D2, when the attachable device 1 is fitted on the finger 11, if the light-emitting diode 22 is on (FIG. 3A1), the photo diode 23 receives light (shown with dashed lines) reflected by the surface of the skin and light (shown with solid lines) returning from inside the body having struck blood capillaries 12 or the like, and a signal waveform is obtained wherein a d.c. component resulting from surface reflection is superposed on a pulse component (FIG. 3A2). When the light-emitting diode 22 is off (FIG. 3B1), because there ceases to be any reflected light, the d.c. component and the pulse component both cease to exist and the signal waveform becomes substantially zero (FIG. 3B2). When the attachable device 1 is not fitted on the finger 11, because the photo diode 23 receives ambient light (FIGS. 3C1, 3D1) whether the light-emitting diode 22 is on or off, the sensor 2 outputs a signal waveform having a d.c. component of the same level in either case (FIGS. 3C2, 3D2).

A determination of attachment state is carried out as described below in (1). However, it may alternatively be carried out as described in (2), in which case the construction for carrying out the determination is simpler.

(1) The d.c. component of the signal waveform outputted by the photo diode 23 when the light-emitting diode 22 is on is compared with the d.c. component of the signal waveform outputted by the photo diode 23 when the light-emitting diode 22 is off. When the d.c. components of the two signal waveforms are of the same level (FIGS. 3C2 and 3D2), it is determined that the attachable device 1 is not fitted on the finger 11. When there is a difference in the d.c. components of the two signal waveforms (FIGS. 3A2, 3B2), it is determined that the attachable device 1 is fitted on the finger 11.

(2) The signal outputted by the photo diode 23 when the light-emitting diode 22 is on is compared with the signal outputted by the photo diode 23 when the light-emitting diode 22 is off. When the two are of the same level (FIGS. 3C2 and 3D2), it is determined that the attachable device 1 is not fitted on the finger 11. When there is a difference between the two (FIGS. 3A2, 3B2), it is determined that the attachable device 1 is fitted on the finger 11.

The operation control circuit 4 is a circuit for controlling the operation of the sensor 2, the transmitting circuit 6 and the attachment detecting circuit 3. This operation control circuit 4 causes the attachment detecting circuit 3 to determine whether or not the attachable device 1 is fitted on the finger 11. When the attachment detecting circuit 3 determines that the attachable device 1 is attached to the finger 11, the operation control circuit 4 supplies operating power to the transmitting circuit 6. The amplifier circuit 5 consists of an operational amplifier or the like. This amplifier circuit 5 amplifies the signal waveform (pulse wave) from the sensor 2 converted to a voltage Value by a current-voltage converter (CVC) 51. The transmitting circuit 6 has an oscillator part, a modulator part and a power amplifier part. This transmitting circuit 6 modulates a carrier wave with the amplified signal waveform into a weak radio wave and transmits this to the pulse wave monitoring unit B, which is disposed remotely. The timer circuit 7 is a circuit in which is stored a time at which the pulse wave is to be sampled or a standby time. When the time at which the pulse wave is to be sampled is reached or the standby time (from a few minutes to several hours) ends and thus it becomes sampling time, the timer circuit 7 supplies operating power to the attachment detecting circuit 3 and the operation control circuit 4.

The pulse wave monitoring unit B has a receiving circuit (REC) 81, an analyzing circuit (AC) 82, a display 83, recording circuit 84 and a reporting circuit 85, and is installed for example in a corner of a sickroom. The receiving circuit 81 is a circuit for demodulating the pulse wave from the modulating wave transmitted from the transmitting circuit 6. The analyzing circuit 82 is a circuit for analyzing the demodulated pulse wave. This analyzing circuit 82 analyzes pulse rate, pulse beat intervals and pulse waveform and so on, and finds any irregular pulse or autonomic nerve abnormality. The display 83 is a liquid crystal display or the like and displays analysis results obtained by the analyzing circuit 82. The recording circuit 84 is a device for holding pulse wave and analysis data on a storage medium along with sample times. The reporting circuit 85 is a circuit for alerting a nurse center or the like when a marked abnormality is found in analysis data.

Figure 4:
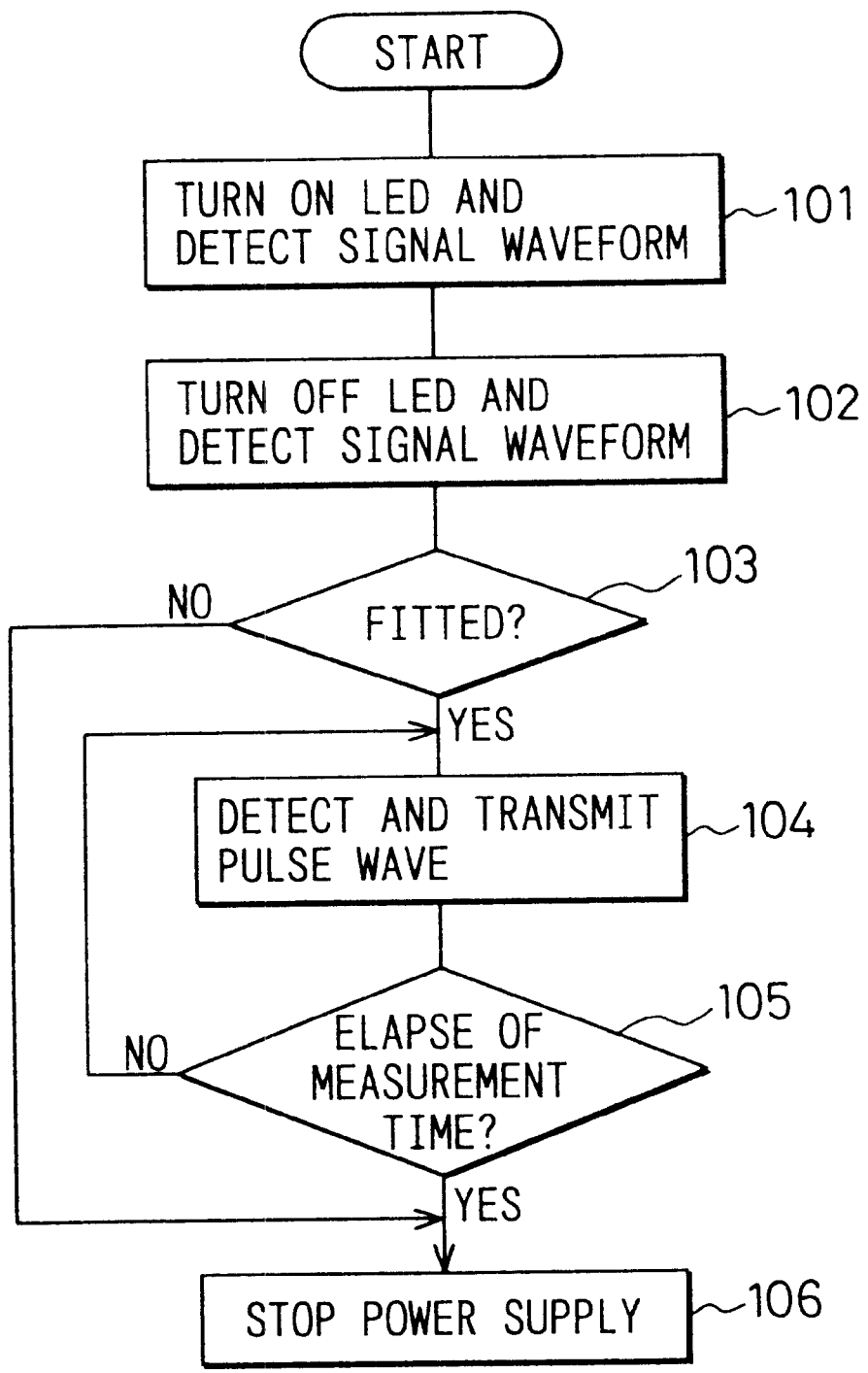
FIG. 4 is a flow chart showing the operation of a pulse wave detecting unit of the pulse wave monitoring system of the first preferred embodiment.

Next, the operation of the pulse wave monitoring system K in measuring the pulse wave of a subject using the pulse wave detecting unit A will be described on the basis of the flow chart of FIG. 4.

At step 101, the operation control circuit 4 passes a current through the light-emitting diode 22 and thereby turns on the light-emitting diode 22, and the attachment detecting circuit 3 detects a signal waveform from the photo diode 23 amplified by the amplifier circuit 5. A step 102, the operation control circuit 4 ceases to pass a current through the light-emitting diode 22 and thereby turns off the light-emitting diode 22, and the attachment detecting circuit 3 again detects a signal waveform from the photo diode 23 amplified by the amplifier circuit 5. The shift from a standby state to step 101 is made on the basis of a measurement time being reached (whereupon the timer circuit 7 supplies operating power to the attachment detecting circuit 3 and the operation control circuit 4) or a test switch 100 being pushed with a pointed object.

At step 103 the attachment detecting circuit 3 determines whether or not the attachable device 1 is fitted. When it determines that it is fitted (YES), processing proceeds to step 104. When it determines that it is not fitted (NO), processing proceeds to step 106. Specifically, the determination of whether or no the attachable device 1 is fitted is carried out by the attachment detecting circuit 3 comparing the d.c. component of the signal waveform obtained when the light-emitting diode 22 is on (the signal waveform obtained at step 101) with the d.c. component of the signal waveform obtained when the light-emitting diode 22 is off (the signal waveform) obtained at step 102). At step 104, the operation control circuit 4 powers the sensor 2, the amplifier circuit 5 and the transmitting circuit 6 and thereby effects detection of a pulse wave and transmits the detected pulse wave to the pulse wave monitoring unit B in the form of a modulated carrier wave. At step 195 it is determined whether or not a measurement time (from a few tens of seconds to several minutes) has elapsed. If the measurement time has elapsed (YES), processing proceeds to step 106. If it has not elapsed (NO), processing returns to step 104 and pulse wave detection and pulse wave transmission are continued. At step 106, the timer circuit 7 stops the supply of power to the other circuits.

After that, the timer circuit 7 finishes counting a predetermined standby time and then the processing of step 101 onward is started again.

According to the first preferred embodiment, the pulse wave detecting unit A is so constructed that, only when the attachment detecting circuit 3 detects that the attachable device 1 is fitted on the finger 11, the operation control circuit 4 supplies operating power to the transmitting circuit 6 and transmits a pulse wave to the pulse wave monitoring unit B. Because of this, the sensor 2 does not pick up external noise and the transmitting circuit 6 does not transmit this noise to the pulse wave monitoring unit B. A pulse wave detected by the sensor 2 with the attachable device 1 fitted on the finger 11 is appropriately transmitted to the pulse wave monitoring unit B. Consequently, erroneous determinations of the pulse wave monitoring unit B can be prevented. Because it is not necessary for an on/off switch for operating the pulse wave detecting unit A at the time of pulse wave detection to be operated, the system is easy to use.

The sensor 2 for detecting the pulse wave doubles, as a sensor for detecting whether or not the attachable device 1 is fitted on the finger 11. Consequently, a special sensor for detecting the attachment state is unnecessary, and the pulse wave detecting device A can be made small.

Because the attachment detecting circuit 3 detects the attachment state by comparing the d.c. component of the signal waveform of the photo diode 23 obtained when the light-emitting diode 22 is on with the d.c. component of the signal waveform of the photo diode 23 obtained when the light-emitting diode 22 is off, the attachment state can be detected accurately with a simple circuit construction.

Because at times of standby the supply of operating power to circuits other than the timer circuit 7 is cut off, the pulse wave of a subject can be checked over a long period without battery replacements having to be carried out.

Further, the standby time is fixed irrespective of whether the attachment device 1 is fitted or not fitted. However, alternatively the standby time of when the attachment device 1 is not fitted may be made longer than the standby time of when the attachable device 1 is fitted. In this case, two timers are provided to count the respective standby times, and the timers are switched between in correspondence with whether or not the attachable device 1 is fitted.

(Second Preferred Embodiment)

A second preferred embodiment of the invention will now be described, with reference to FIGS. 5A and 5B through FIG. 8.

Figure 5A:
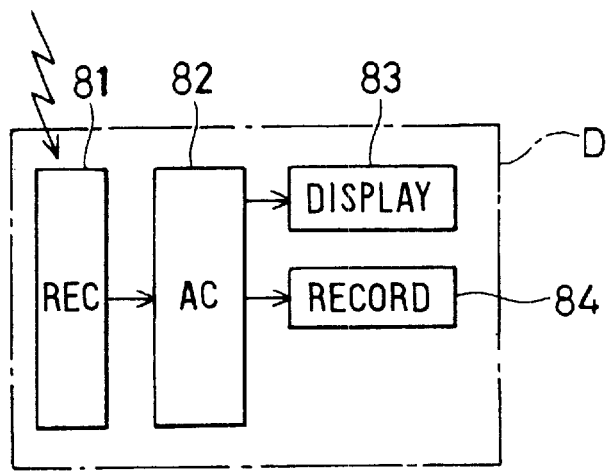
FIG. 5A is a block diagram of an analyzing unit and FIG. 5B a schematic view of a pulse wave detecting unit of a pulse wave analyzing system of a second preferred embodiment of the invention.
Figure 5B:
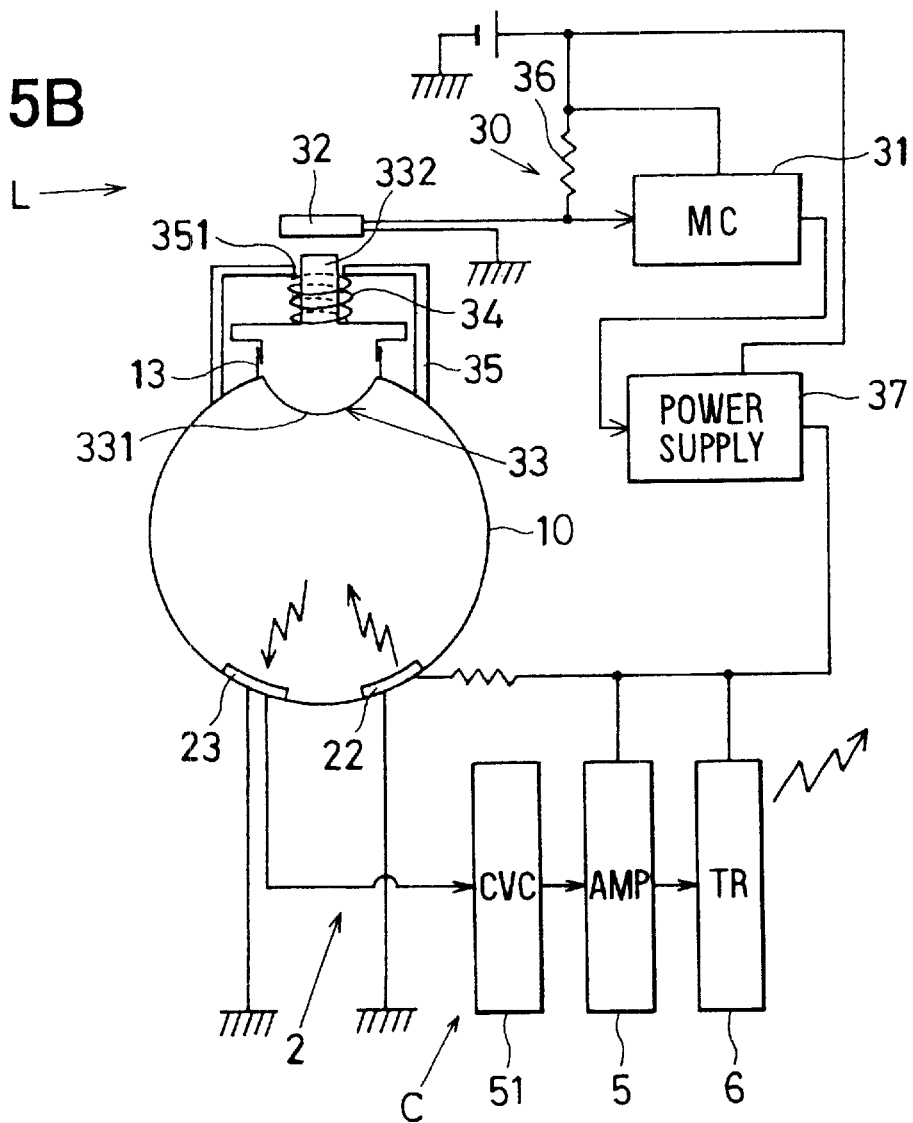

As shown in FIGS. 5A and 5B, a pulse wave analyzing system L is made up of a pulse wave detecting unit C, having a finger insertion cylinder 10, a signal detection sensor 2 and an amplifier circuit 5, an insertion detection circuit 30 for attachment state detection, and a power supply circuit 37 constituting part of a processing alteration circuit, and a pulse wave analyzing unit D for analyzing a pulse wave.

The pulse wave detecting unit C is built into an easily carryable housing, and for checking a pulse wave it is placed on a table or the like at the side of a bed in which a human subject is lying.

The finger insertion cylinder 10, which is made of plastic, is a cylinder mounted on the top of the pulse wave detecting unit C, and has an internal diameter such that a base part 111 of a finger 11 of a subject will just fit in it. A surface treatment such as painting black for preventing the reflection of light is carried out on the inside of this finger insertion cylinder 10.

The sensor 2 comprises a light-emitting diode 22 and a photo diode 23. Light emitted by the light-emitting diode 22 passes through the skin of the finger 11 into the finger, reaches blood capillaries 12 and is partly absorbed and partly scattered by reflection and returned from inside the finger. The photo diode 23 is disposed at the bottom of the inside of the attachable device 1 where it can receive this returning light.

The amplifier circuit 5 consists of an operational amplifier or the like. This amplifier circuit 5 amplifies the signal waveform (pulse wave) from the photo diode 23 converted to a voltage Value by a current-voltage converter circuit 51. The transmitting circuit 6 has an oscillator port, a modulator part and a power amplifier part. This transmitting circuit 6 modulates a carrier wave with the amplified signal waveform into a weak radio wave and transmits this to the pulse wave analyzing unit D, which is disposed remotely.

Figures 6, 8:
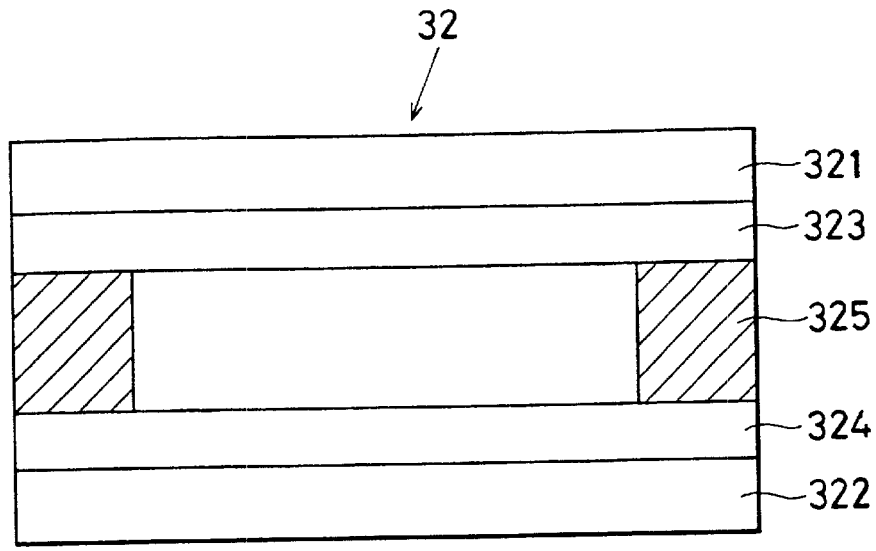
FIG. 6 is a sectional view showing a switch used in the pulse wave detecting unit of the pulse wave analyzing system of the second preferred embodiment.
FIG. 8 is a table illustrating a display of the analyzing unit of the pulse wave analyzing system of the second preferred embodiment.

The insertion detection circuit 30 is made up of a microcomputer 31, a switch 32, a planar 33, a spring 34, a plunger case 35 and a resistor 36. It determines whether or not the finger 11 has been inserted into the finger insertion cylinder 10. The switch 32, as shown in FIG. 6, is made up of base films 321 and 322, electrodes 232 and 324 affixed to the rear sides of the base films 321 and 322, and a spacer film 325 disposed between the electrodes 323 and 324. This switch 32 is fixed over a circular hole 351, which will be further discussed later. The plunger 33 is made up of a spherical part 331 (shaped to not damage the finger 11) fitted displaceably up and down in a cylindrical part 13 of the finger insertion cylinder 10 and having a lower face which abuts with the upper side of the finger 11, and a rod part 332 on which is fitted a spring 34. The plunger case 35 is mounted on the top part of the finger insertion cylinder 10, and the circular hole 351, from which the rod part 332 projects, is provided in the top face of the plunger case 35.

Normally, because the spring 34 urges the plunger 33 downward, the rod part 332 of the plunger 33 does not push the switch 32, there is no continuity between the electrodes 323 and 324, and a voltage V across the electrodes assumes a high level. In this case, the microcomputer 31 determines that the finger 11 has not been inserted into the finger insertion cylinder 10. When the finger 11 is inserted into the finger insertion cylinder 10, because the plunger 33 shifts upward and the rod part 332 pushes the switch 32, the electrodes 323 and 324 become continuous and the voltage V across the two assumes a low level. In this case, the microcomputer 31 determines that the finger 11 has been inserted into the finger insertion cylinder 10 and outputs a control signal to the power supply circuit 37.

The power supply circuit 37 is a circuit for controlling a power supply to the amplifier circuit 5, the transmitting circuit 6 and the light-emitting diode 22. This power supply circuit 37 starts the power supply when it inputs the control signal from the microcomputer 31.

When during analysis of the pulse wave the finger 11 is removed from the finger insertion cylinder 10, because the microcomputer 31 determines that the finger 11 is not inserted in the finger insertion cylinder 10, the power supply circuit 37 cuts off the power supply to the amplifier circuit 5, the transmitting circuit 6 and the light-emitting diode 22.

The pulse wave analyzing unit D has a receiving circuit 81, an analyzing circuit 82, a display 83 and recording circuit 84, and is installed for example in a corner of a sickroom. This receiving circuit 81 is a circuit for demodulating the pulse wave from the modulated wave transmitted from the transmitting circuit 6. The analyzing circuit 82 is a circuit for analyzing the demodulating pulse wave, and alters a part of processing. On the basis of the pulse wave, this analyzing circuit 82 computes and analyzes parameters (pulse rate, pulse beat intervals and pulse waveforms) manifesting the state of the body, and checks for any irregular pulse or autonomic nerve abnormality. The analyzing circuit 82 does not carry out computation of the parameters based on the pulse wave until the pulse wave is demodulated, while the detection of insertion/non-insertion of the finger 11 into the finger insertion cylinder 10 is being carried out.

The display 83 is a liquid crystal display or the like and displays the insertion state of the finger 11 and analysis results obtained by the analyzing circuit 82. The recording circuit 84 is a device for holding pulse wave and analysis data on a storage medium along with sample times.

Figure 7A:
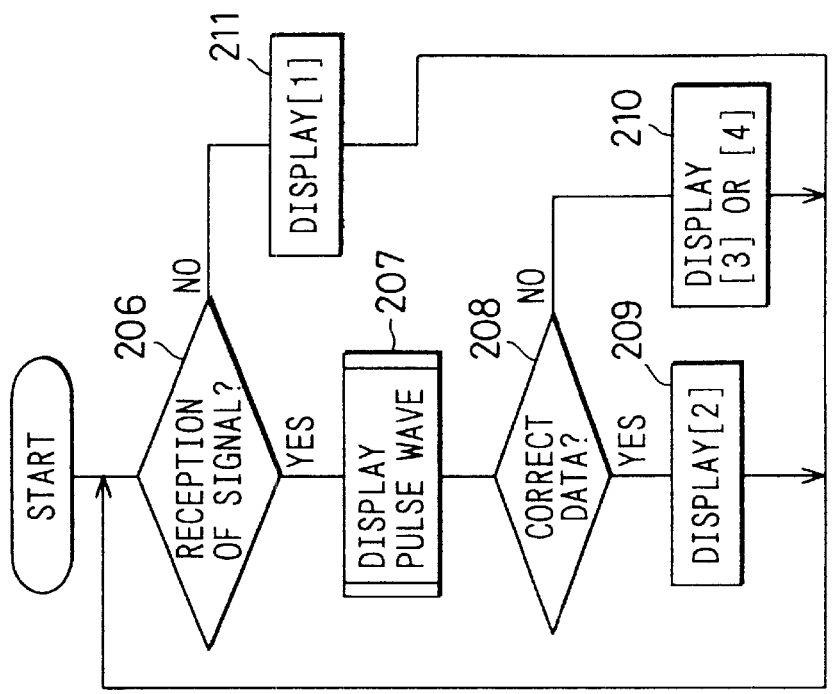
FIGS. 7A and 7B are flow charts showing the operation of the pulse wave analyzing system of the second preferred embodiment.
Figure 7B:
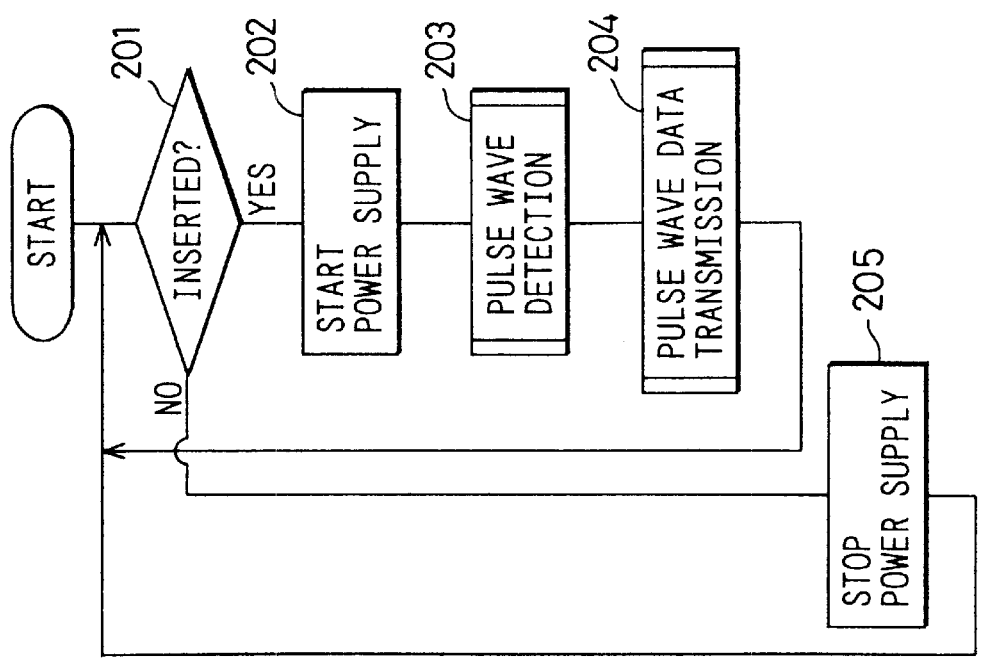

Next, the operation of a pulse wave analyzing system L for analyzing the pulse wave of a subject using the pulse wave detecting unit C will be described, with reference to the flow charts of FIGS. 7A and 7B.

In a signal transmitter side, at step 201, on the basis of the voltage V, the microcomputer 31 determines whether or not the finger 11 has been inserted into the finger insertion cylinder 10. When it determines that it has been so inserted (YES), processing proceeds to step 202. When it determines that the finger 11 has not been inserted (NO), processing proceeds to step 205.

At step 202, the power supply circuit 37 starts the power supply to the amplifier circuit 5, the transmitting circuit 6 and the light-emitting diode 22. As a result, pulse wave detection processing (step 203) and pulse wave data transmission processing (step 204) are executed.

At step 205, the power supply circuit 37 stops the power supply to the amplifier circuit 5, the transmitting circuit 6 and the light-emitting diode 22. The power supply to the microcomputer 31 and the power supply circuit 37 is always on.

The pulse wave detection processing and pulse wave data transmission processing described above are carried out at predetermined intervals (from a few tens of seconds to several tens of minutes), using a timer built into the microcomputer 31.

At a signal receiver side, at step 206, it is determined whether or not a modulated wave is being received. When a modulated wave is being received (YES), processing proceeds to step 207. When a modulated wave is not being received (NO), processing proceeds to step 211.

At step 207 the waveform of the pulse wave is displayed on the display 83, and processing proceeds to step 208. At step 208, the analyzing circuit 82 analyzes the waveform of the pulse wave. When it is normal (YES), processing proceeds to step 209. When it is abnormal (NO), processing proceeds to step 210.

As shown in [2] of FIG. 8, at step 209, "Normal" is displayed on the display 83 (Display 2). As shown in [3] and [4] of FIG. 8, at step 210, a type of abnormality, such as "Fast Beats" "Missing Beats", or "Noise Ingress" (Display 3, 4), is displayed on the display 83. As shown in [1] of FIG. 8, at step 211, "Finger Not Inserted" (Display 1) is displayed on the display 83.

According to the second preferred embodiment, the pulse wave detecting unit C of the pulse wave analyzing system L is so constructed that when the microcomputer 31 detects that the finger 11 is inserted in the finger insertion cylinder 10, the operation control circuit 4 supplies operating power to the light-emitting diode 22, the amplifier circuit 5 and the transmitting circuit 6. Because of this, since detection of the pulse wave and transmission of the pulse wave are only carried out after the finger 11 is inserted, the problem of the photo diode 23 picking up external noise (ambient light) and the transmitting circuit 6 transmitting this noise to the pulse wave analyzing unit D does not arise. Thus, a pulse wave detected with the finger 11 inserted in the finger insertion cylinder 10 is appropriately transmitted to the pulse wave analyzing unit D. Therefore, erroneous determinations of the pulse wave analyzing unit D can be prevented. Because a start switch for operating the pulse wave detecting unit C at the time of pulse wave detection is not necessary, the system is easy to use. Because at times of standby operating power is not supplied to the light-emitting diode 22, the amplifier circuit 5 and the transmitting circuit 6, the standby power of the pulse wave detecting unit C side can be reduced.

(Third Preferred Embodiment)

Figure 9:
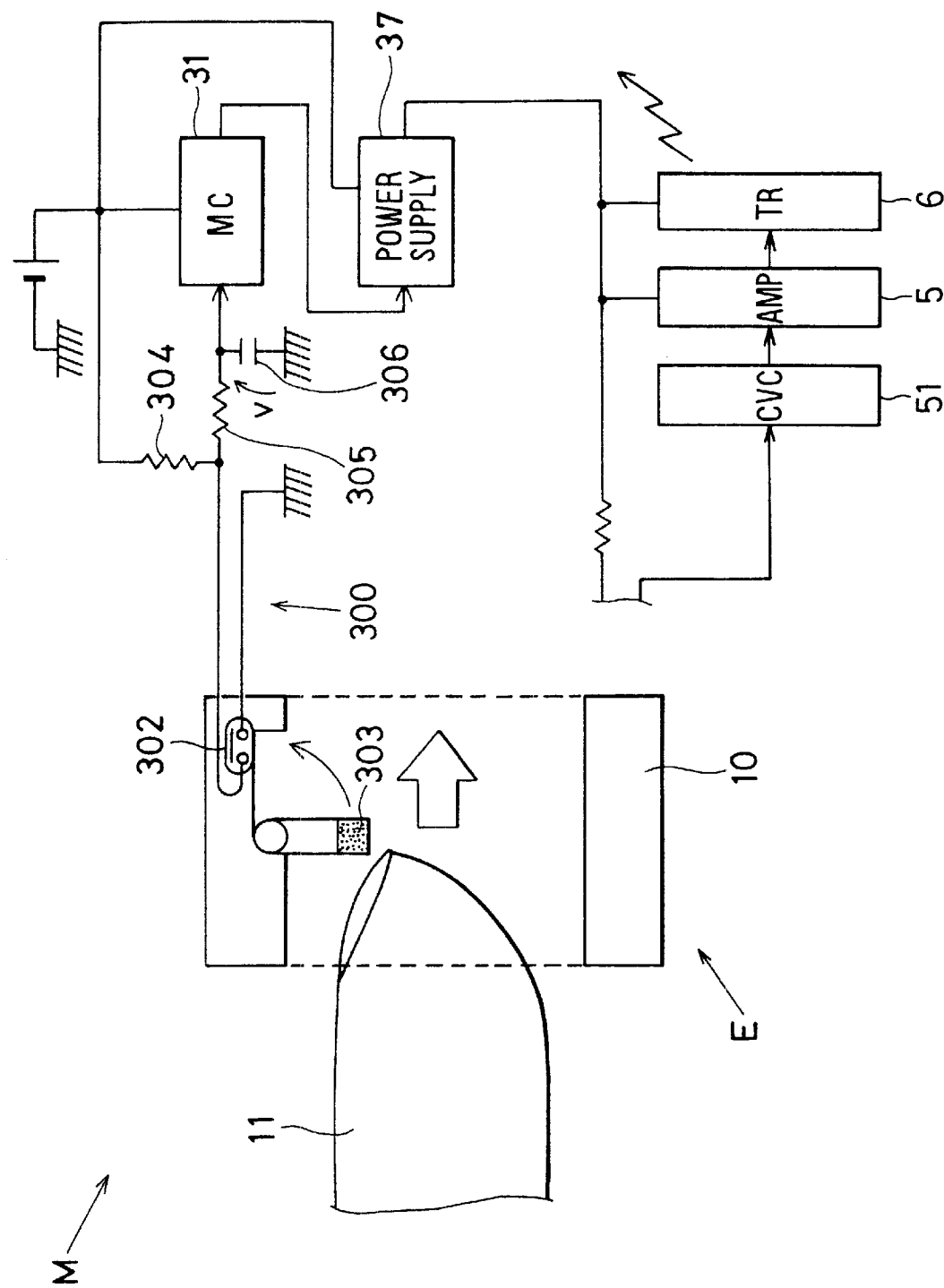
FIG. 9 is a schematic view showing a pulse wave detecting unit of a pulse wave analyzing system of a third preferred embodiment of the invention.

A third preferred embodiment of the invention will now be described, with reference to FIG. 9. As shown in FIG. 9, a pulse wave analyzing system M is made up of a pulse wave detecting unit E and a pulse wave analyzing unit D shown in FIG. 5A for analyzing a pulse wave.

In this embodiment, an insertion detection circuit 300 is made up of a microcomputer 31, a reed switch 302, a magnet 303, resistors 304 and 305, and a capacitor 306. The reed switch 302 is disposed at the top of the inside of the finger insertion cylinder 10, slightly behind the entrance of the finger insertion cylinder 10, and is connected to a point of connection between the resistors 304 and 305. The magnet 303 is mounted at the top of the inside of the finger insertion cylinder 10 on the side of the reed switch 302 nearer to the entrance of the finger insertion cylinder 10. This magnet 303 is caused to swing toward the reed switch 302 when a finger 11 is inserted into the finger insertion cylinder 10.

Normally, because the contacts of the reed switch 302 are OFF, a voltage V across them is at a high level. In this case, the microcomputer 31 determines that the finger 11 has not been inserted into the finger insertion cylinder 10. When the finger 11 is inserted into the finger insertion cylinder 10, on the other hand, the magnet 303 swings toward the reed switch 302 and turns ON the reed switch 302, whereupon the voltage V assumes a low level. In this case, the microcomputer 31 determines that the finger 11 has been inserted into the finger insertion cylinder 10.

(Fourth Preferred Embodiment)

Figure 10:
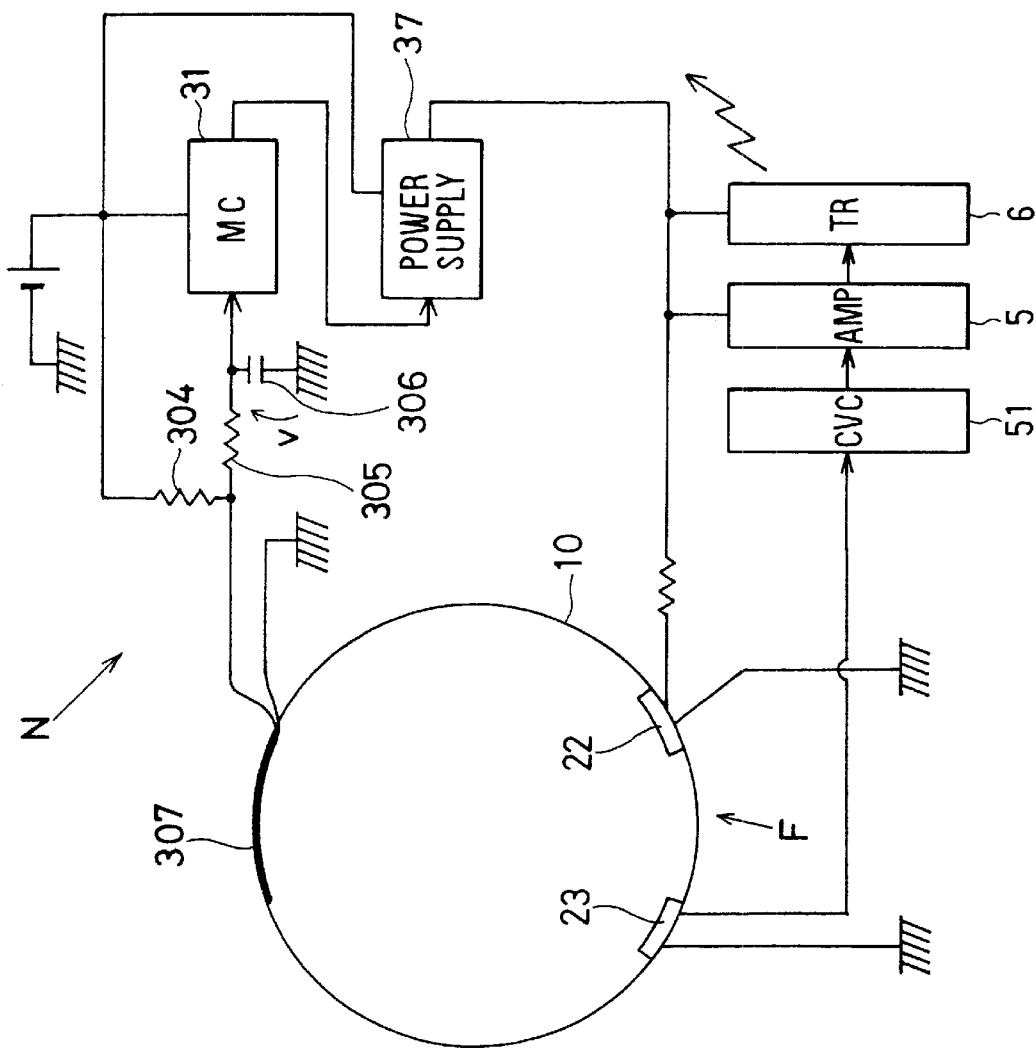
FIG. 10 is a schematic view showing a pulse wave detecting unit of a pulse wave analyzing system of a fourth preferred embodiment of the invention.

A fourth preferred embodiment of the invention will now be described, with reference to FIG. 10. As shown in FIG. 10, a pulse wave analyzing system N is made up of a pulse wave detecting unit F and a pulse wave analyzing unit D shown in FIG. 5A for analyzing a pulse wave.

In this embodiment, an insertion detection circuit 300 is made up of a microcomputer 31, a film switch 307, resistors 304 and 305, and a capacitor 306. The film switch 307 is disposed at the top of the inside of the finger insertion cylinder 10, slightly behind the entrance of the finger insertion cylinder 10, and is connected to a point of connection between the resistors 304 and 305.

Normally, because the contacts of the film switch 307 are OFF, a voltage V across them is at high level. In this case, the microcomputer 31 determines that the finger 11 has not been inserted into the finger insertion cylinder 10. When the finger 11 is inserted into the finger insertion cylinder 10, pressure of the finger turns ON the contacts of the film switch 307, and the voltage V assumes a low level. In this case, the microcomputer 31 determines that the finger 11 has been inserted into the finger insertion cylinder 10.

(Fifth Preferred Embodiment)

Figure 11:
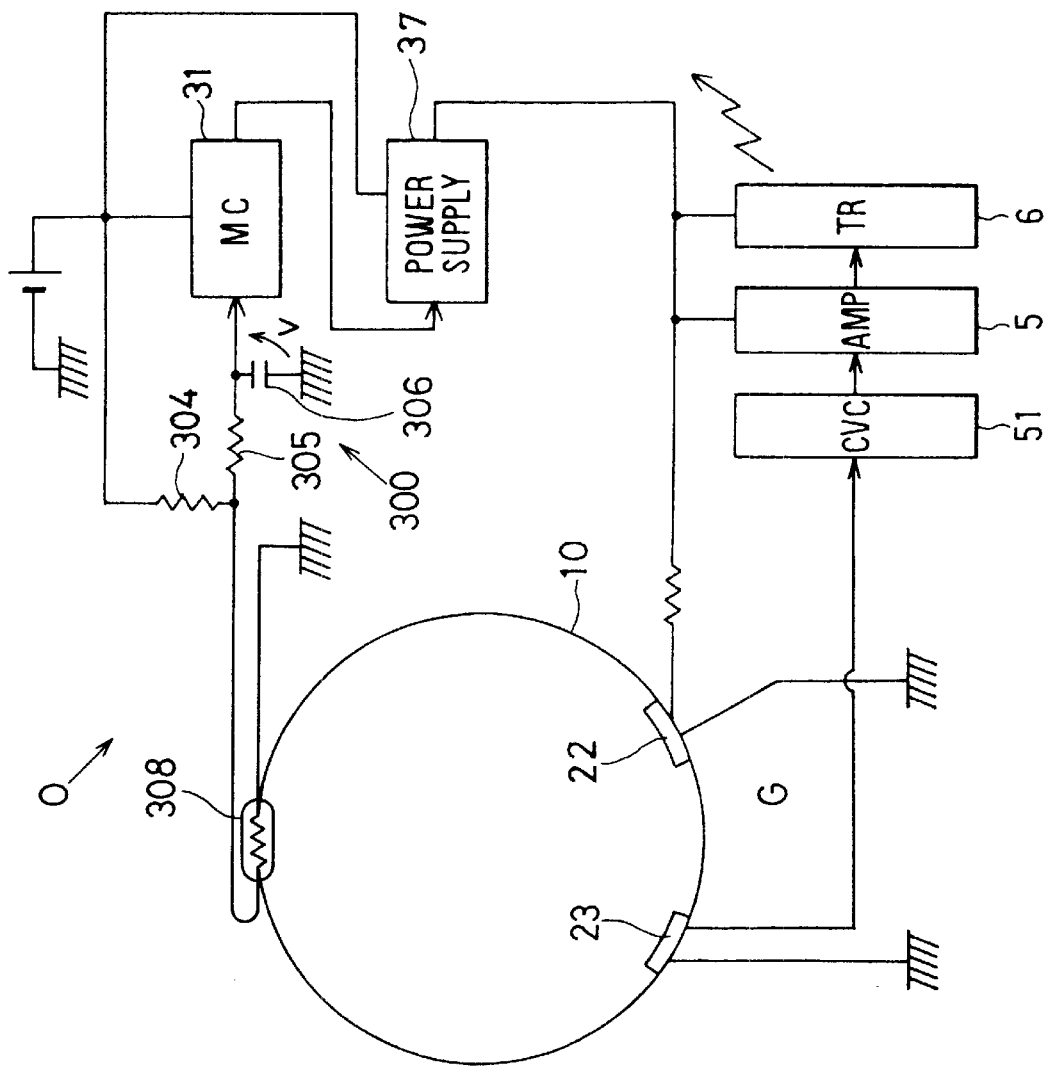
FIG. 11 is a schematic view showing a pulse wave detecting unit of a pulse wave analyzing system of a fifth preferred embodiment of the invention.

A fifth preferred embodiment of the invention will now be described, with reference to FIG. 11. As shown in FIG. 11, a pulse wave analyzing system O is made up of a pulse wave detecting unit G and a pulse wave analyzing unit D shown in FIG. 5A for analyzing a pulse wave.

In this embodiment, an insertion detection circuit 300 is made up of a microcomputer 31, a thermistor 308, resistors 304 and 305, and a capacitor 306. The thermistor 308 is disposed at the top of the inside of the finger insertion cylinder 10, slightly behind the entrance of the finger insertion cylinder 10, and is connected to a point of connection between the resistors 304 and 305.

Normally, because the thermistor 308 detects room temperature, a voltage V is at a level corresponding to the detected room temperature. In this case, the microcomputer 31 determines that the finger 11 has not been inserted into the finger insertion cylinder 10. When the finger 11 is inserted into the finger insertion cylinder 10, the thermistor 308 is warmed by body heat and the voltage V changes. In this case, the microcomputer 31 determines that the finger 11 has been inserted into the finger insertion cylinder 10.

(Sixth Preferred Embodiment)

Figure 12:
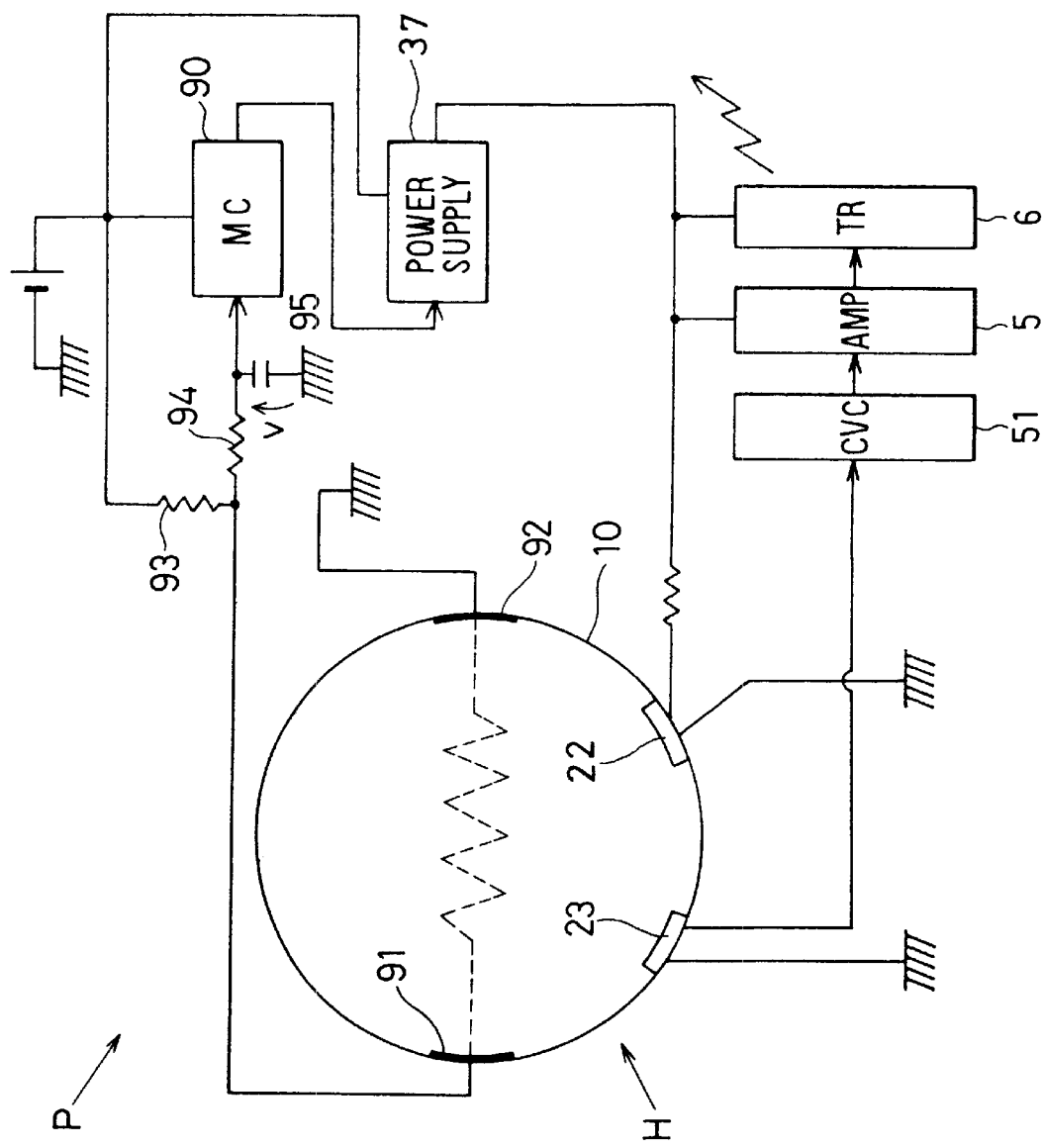
FIG. 12 is a schematic view showing a pulse wave detecting unit of a pulse wave analyzing system of a sixth preferred embodiment of the invention.

A sixth preferred embodiment of the invention will now be described, with reference to FIG. 12. As shown in FIG. 12, a pulse wave analyzing system P is made up of a pulse wave detecting unit H and a pulse wave analyzing unit D shown in FIG. 5A for analyzing a pulse wave.

In this embodiment, an insertion detection circuit 9 is made up of a microcomputer 90, electrodes 91 and 92, resistors 93 and 94, and a capacitor 95. The electrodes 91 and 92 are disposed centrally on either inner side of the finger insertion cylinder 10, slightly behind the entrance of the finger insertion cylinder 10. One end of the pair is connected to a point of connection between the resistors 93 and 94.

Normally, because there is an infinite resistor between the electrodes 91 and 92, the voltage V is approximately the power supply voltage. In this case, the microcomputer 90 determines that the finger 11 has not been inserted into the finger insertion cylinder 10. When the finger 11 is inserted into the finger insertion cylinder 10, because the voltage at the point of connection between the resistors 93 and 94 is divided by the resistor 93 and the electrical resistor of the finger) between the electrodes 91 and 92, the voltage V falls. In this case, the microcomputer 90 determines that the finger 11 has been inserted into the finger insertion cylinder 10.

(Seventh Preferred Embodiment)

Figure 13:
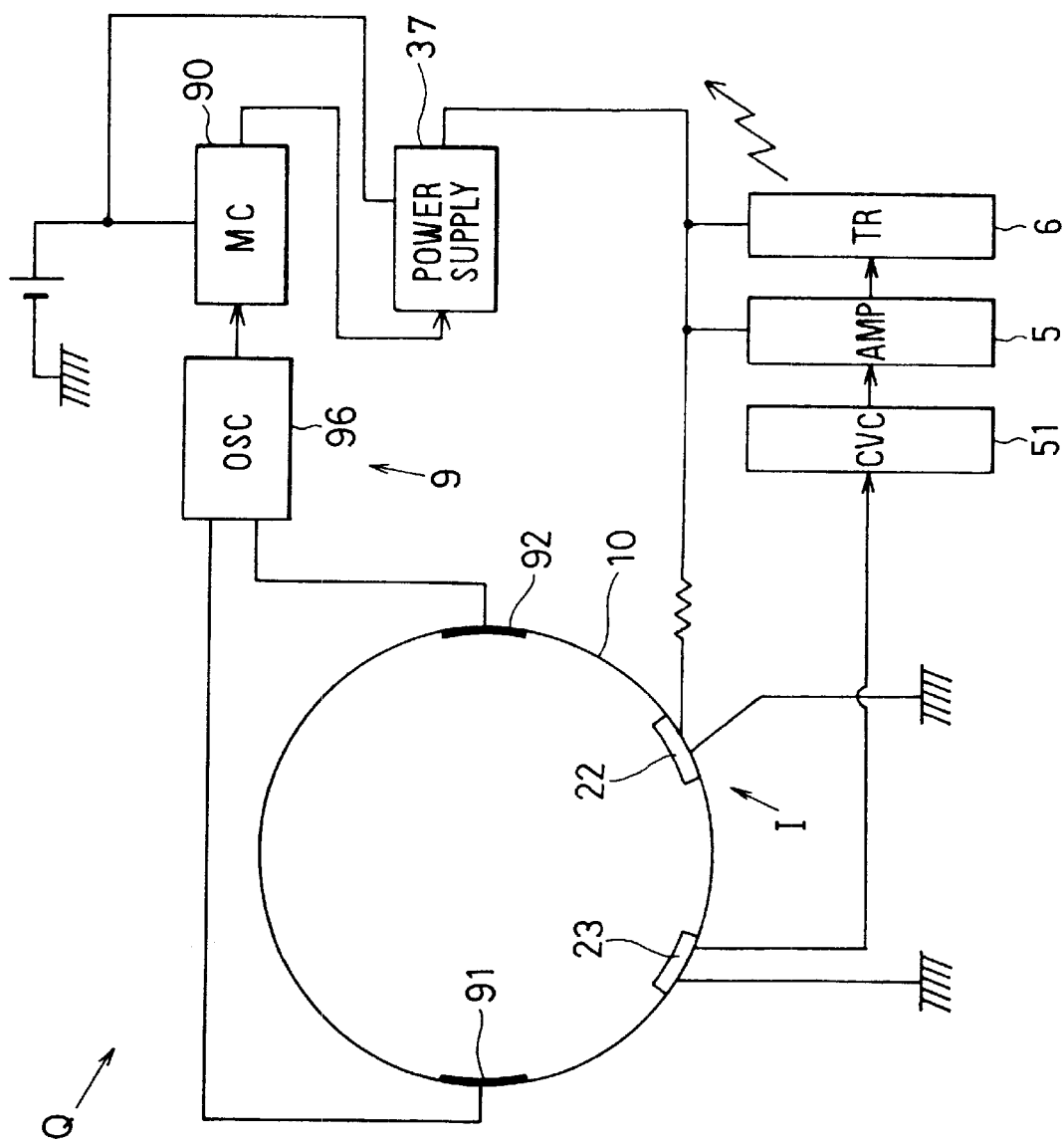
FIG. 13 is a schematic view showing a pulse wave detecting unit of a pulse wave analyzing system of a seventh preferred embodiment of the invention.

A seventh preferred embodiment of the invention will now be described with reference to FIG. 13. As shown in FIG. 13, a pulse wave analyzing system Q is made up of a pulse wave detecting unit I and a pulse wave analyzing unit D shown in FIG. 5A for analyzing a pulse wave.

In this embodiment, an insertion detection circuit 9 is made up of a microcomputer 90, electrodes 91 and 92, and an oscillator circuit (OSC) 96. The electrodes 91 and 92 are disposed centrally on either inner side of the finger insertion cylinder 10, slightly behind the entrance of the finger insertion cylinder 10. The oscillator circuit 96 is a circuit for oscillating at a high frequency determined by the capacitance across the electrodes 91 and 92.

When the finger 11 is inserted into the finger insertion cylinder 10, because the static capacitance between the electrodes 91, 92 changes, the oscillating frequency of the oscillator circuit 96 changes. On the basis of this, the microcomputer 90 determines that the finger 11 has been inserted into the finger insertion cylinder 10.

(Eighth Preferred Embodiment)

Figure 14:
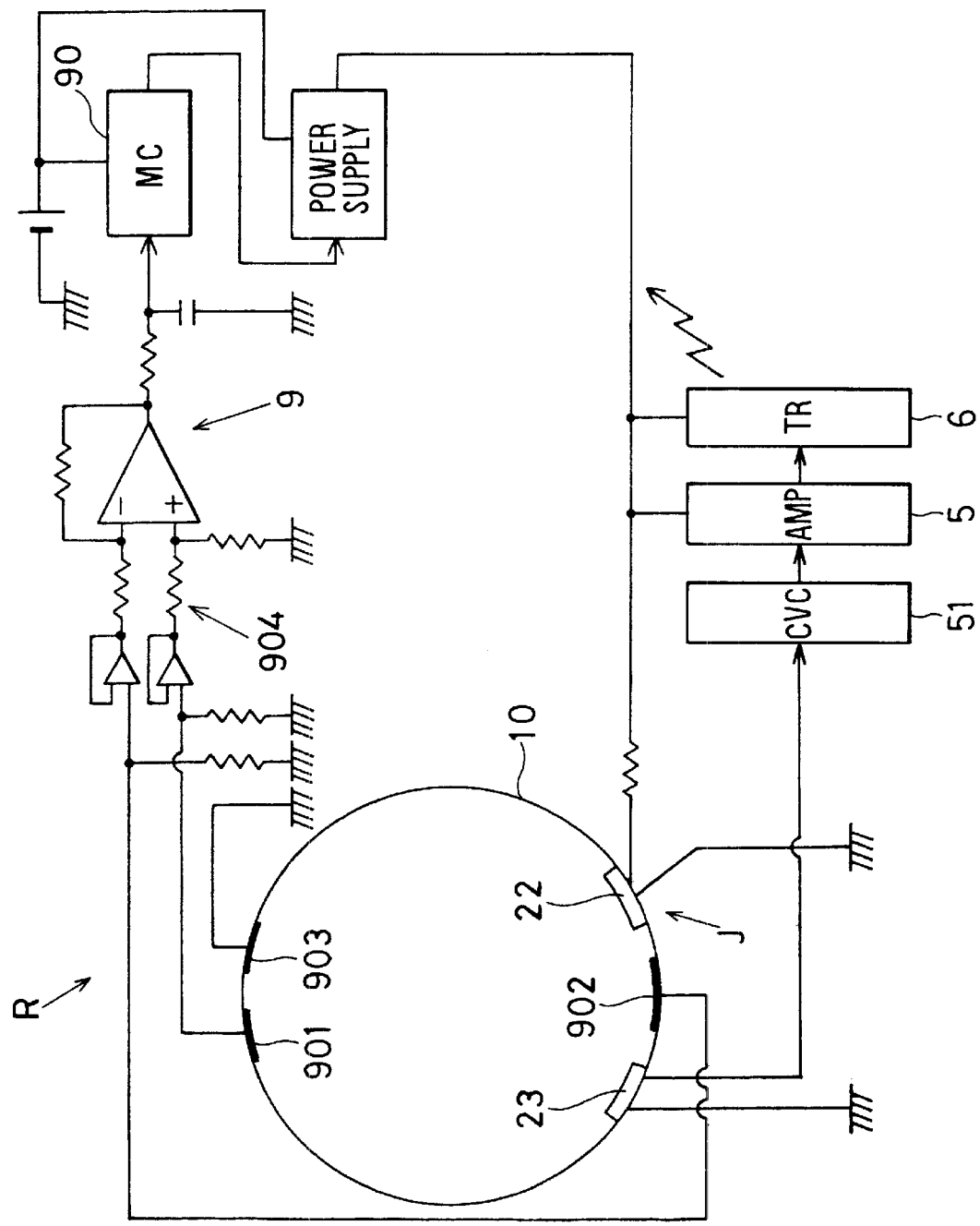
FIG. 14 is a schematic view showing a pulse wave detecting unit of a pulse wave analyzing system of an eighth preferred embodiment of the invention.

An eighth preferred embodiment of the invention will now be described with reference to FIG. 14. As shown in FIG. 14, a pulse wave analyzing system R is made up of a pulse wave detecting unit J and a pulse wave analyzing unit D shown in FIG. 5A for analyzing a pulse wave.

In this embodiment, an insertion detection circuit 9 is made up of a microcomputer 90, electrodes 901, 902 and 903, and a skin potential detecting circuit 904. The electrodes 901 and 903 are disposed at the top of the inside of the finger insertion cylinder 10, slightly behind the entrance of the finger insertion cylinder 10. The electrode 902 is disposed at the bottom of the inside of the finger insertion cylinder 10, slightly behind the entrance of the finger insertion cylinder 10.

The skin potential detecting circuit 904 comprises an operational amplifier or the like, and amplifies the voltage between the electrodes. When the finger 11 is inserted into the finger insertion cylinder 10, because a voltage of several tens of mV arises across the electrodes 901 and 902 due to skin voltage, the microcomputer 90 determines that the finger 11 has been inserted into the finger insertion cylinder 10.

It is to be noted in the above embodiments that transmission of the pulse wave from the vital signal detecting device to the vital signal monitoring unit can be effected using connecting wires, instead of by wireless transmission using radio waves, ultrasound or light. When the attachable device is not attached to the body of a subject, the signal transmission to the vital signal monitoring system may be stopped by cutting off or shorting the signal waveform from the sensor. The attachable device may alternatively be a band made of rubber or may be of a form to be affixed to a human body.

(Ninth Preferred Embodiment)

Figure 15:
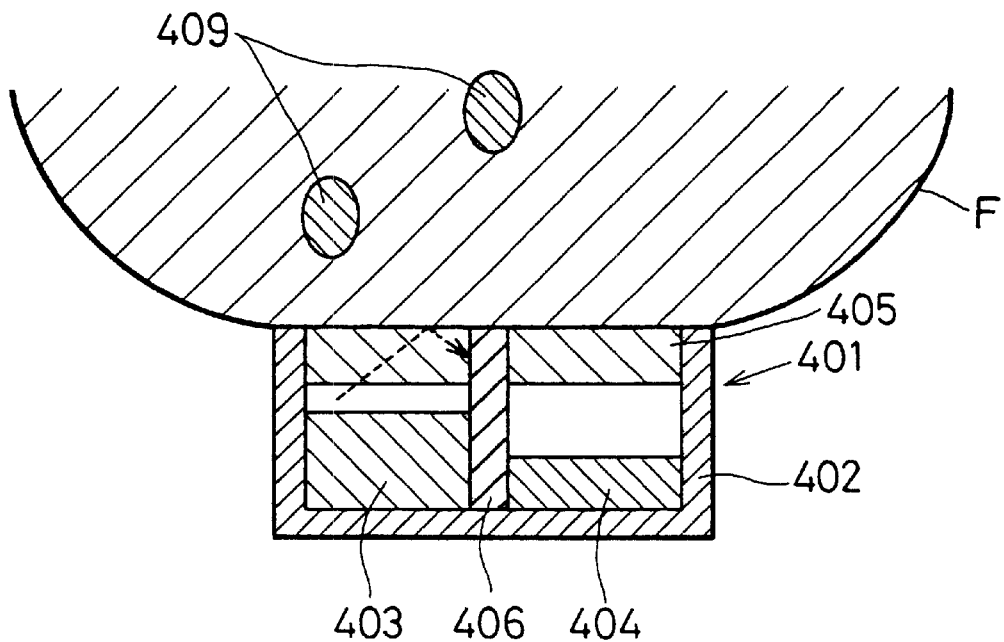
FIG. 15 is a sectional view of a pulse wave sensor constituting a ninth preferred embodiment of the invention.
Figure 16:
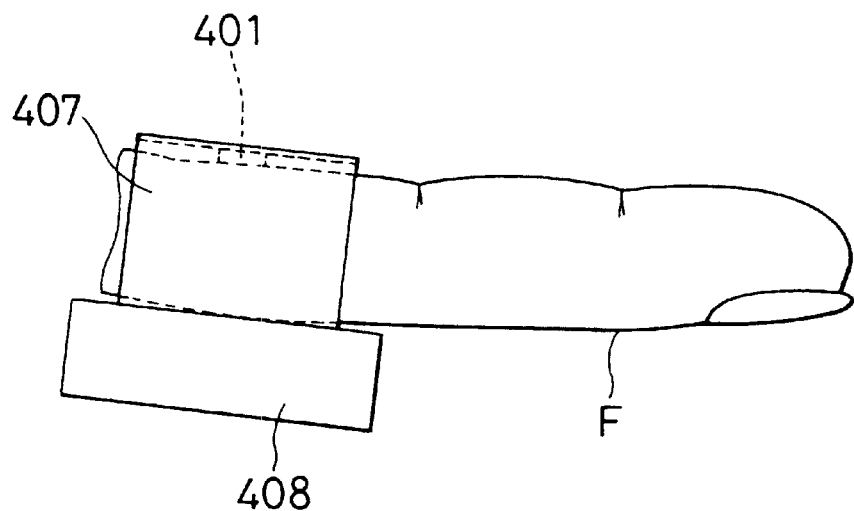
FIG. 16 is a view showing the pulse wave sensor in use.

A pulse wave sensor 401 of this preferred embodiment, as shown in FIG. 15, is made up of a package 402 having an opening in an upper face, a light-emitting device (light-emitting diode) 403 and a light-receiving device (photo diode) 404 received in this package 402, a light-transmitting plate 405, and a light-blocking member 406 disposed between the light-emitting device 403 and the light-receiving device 404. As shown in FIG. 16, the pulse wave sensor 401 is used by being attached to a finger F of a human subject with a fixing belt 407.

A circuit board (not shown) is fixed inside the package 402, and the light-emitting device 403 and the light-receiving device 404, which are electronic components, are mounted side by side on this circuit board. The light-transmitting plate 405, through which light can pass, is for example a glass plate, and a light-emitting device side and a light-receiving device side of the light-transmitting plate 405 are divided by the light-blocking member 406. The light-blocking member 406, through which light cannot pass, is provided as a plate having a predetermined thickness and is interposed between the light-emitting device 403 and the light-receiving device 404 and divides the light-transmitting plate 405 and the inside of the package 402 into a light-emitting device side and a light-receiving device side, as shown in FIG. 15.

The fixing belt 407 has a belt width such that it can cover an area around the pulse wave sensor 401 to a radius of 8 mm, to prevent extraneous light from entering the light-receiving device 404. A circuit part 408 connected by signal wires (not shown) to the circuit board of the pulse wave sensor 401 is mounted on the fixing belt 407. This circuit part 408 has an amplifier circuit and a transmitter circuit and can amplify and transmit to a separate receiver a detection signal sent to it through the signal wires from the pulse wave sensor 401.

In this embodiment, some of the light emitted from the light-emitting device 403 strikes blood capillaries 409 passing through the inside of the finger F and is absorbed by haemoglobin in the blood flowing through the blood capillaries 409. The rest of the light is reflected and scattered by the blood capillaries 409, and some of this reflected light enters the light-receiving device 404. Here, because the amount of haemoglobin in the blood capillaries 409 varies in a wave pattern due to pulsation of the blood, the amount of light absorbed by the haemoglobin also varies in a wave pattern. As a result, the light reflected by the blood capillaries 409 and entering the light-receiving device 404 also varies, and this variation causes pulse waves.

It may happen that some of the light emitted from the light-emitting device 403 is reflected by the interface between the surface of the light-transmitting plate 405 and the skin surface of the finger F and returns to the light-transmitting plate 405. In this case, if light reflected at that interface enters the light-receiving device 404, it is difficult for the pulse wave to be measured correctly. However, with respect to this, in the pulse wave sensor 401 of this preferred embodiment, because the light-transmitting plate 405 is divided into the light-emitting device side and the light-receiving device side by the light-blocking member 406 and the light-blocking member 406 is also disposed between the light-emitting device 403 and the light-receiving device 404, light emitted from the light-emitting device 403 which is then reflected at the above interface can be prevented by the light-blocking member 406 from entering the light-receiving device 404 side. As a result, because as shown in FIG. 15 light reflected at that interface does not directly enter the light-receiving device 404 and the influence of such reflected light on pulse wave measurement can be eliminated, the detection capability can be increased.

Preferably, at least the surface of the light-blocking member 406 on the light-receiving device side thereof is made black. In this case, because the amount of light reflected at the surface of the light-blocking member 406 is reduced, the probability of noise light entering the light-receiving device 404 can be reduced.

The surface of the light-blocking member 406 on the light-emitting device side thereof may be given a mirror finish. In this case, not only is light reflected at the interface blocked, but also, because light emitted from the light-emitting device 403 is effectively projected into the human body by the mirror surface, there is also the effect that the detection sensitivity can be increased.

Whereas in this preferred embodiment a circuit part 408 is provided on a fixing belt 407 and a detection signal is transmitted from the circuit part 408 to a receiver, alternatively for example a wristwatch-type pulse wave measuring device with a built-in microcomputer may be provided, and this measuring device connected to the pulse wave sensor 401 directly by lead wires.

(Tenth Preferred Embodiment)

Figure 17:
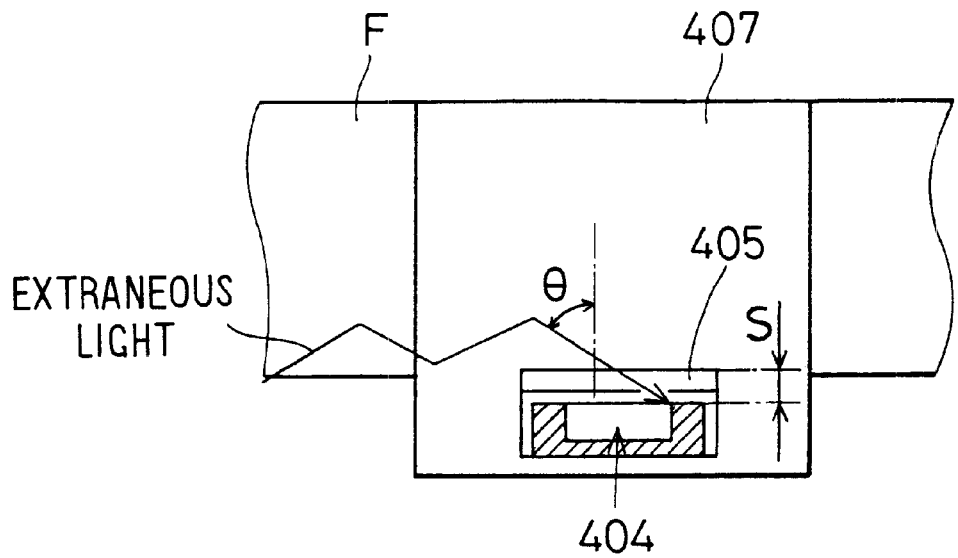
FIG. 17 is a schematic view of a pulse wave sensor constituting a tenth preferred embodiment, wherein a light-receiving device is lowered with respect to a light-transmitting plate.

In the pulse wave sensor 401 of this preferred embodiment, as shown in FIG. 17, the light-receiving device 404 is disposed at a position lower than the light-transmitting plate 405 to reduce extraneous light entering the light-receiving device 404 through the finger F as a light guide. That is, the light-receiving device 404 is disposed away from the light-transmitting plate 405 and a predetermined distance s (for example 0.5 to 2 mm) is provided between the surface of the light-transmitting plate 405 and the light-receiving face of the light-receiving device 404. When sunlight or light from a fluorescent light (extraneous light) enters the light-receiving device 404, it can be considered to have reached the light-receiving device 404 by being guided by the skin of the finger F. Therefore, by disposing the light-receiving device 404 at the lower position with respect to the light-transmitting plate 405, because the angle of incidence θ at which light is able to reach the light-receiving device 404 through the light-transmitting plate 405 decreases, extraneous light having a large angle of incidence θ such as that guided through the skin of the finger F can be blocked. As a result, erroneous detection caused by the influence of extraneous light can be reduced and the detection capability can be increased.

However, in the case of this preferred embodiment, preferably only the light-receiving device 404 is disposed lowered with respect to the light-transmitting plate 405, and the light-emitting device 403 is disposed as close as possible to the light-transmitting plate 405. When the light-emitting device 403 is close to the light-transmitting plate 405, light emitted from the light-emitting device 403 is projected into the human body effectively and the detection sensitivity increases because the light path length from the light-emitting device 403 to the blood capillaries 409 of the finger F is made smaller.

Of course, by combining the tenth preferred embodiment and the ninth preferred embodiment as shown in FIG. 15, the respective effects of both preferred embodiments can be obtained together.

(Eleventh Preferred Embodiment)

Figure 18:
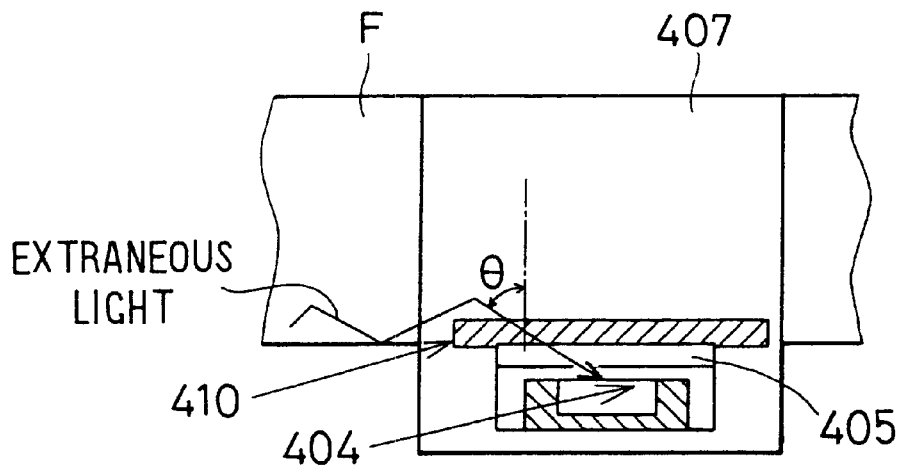
FIG. 18 is a schematic view of a pulse wave sensor constituting an eleventh preferred embodiment, wherein a light control film is used.

In this embodiment, the pulse wave sensor 401 has a light control film 410 that is disposed above the light-receiving device 404, as shown in FIG. 18.

Figure 19:
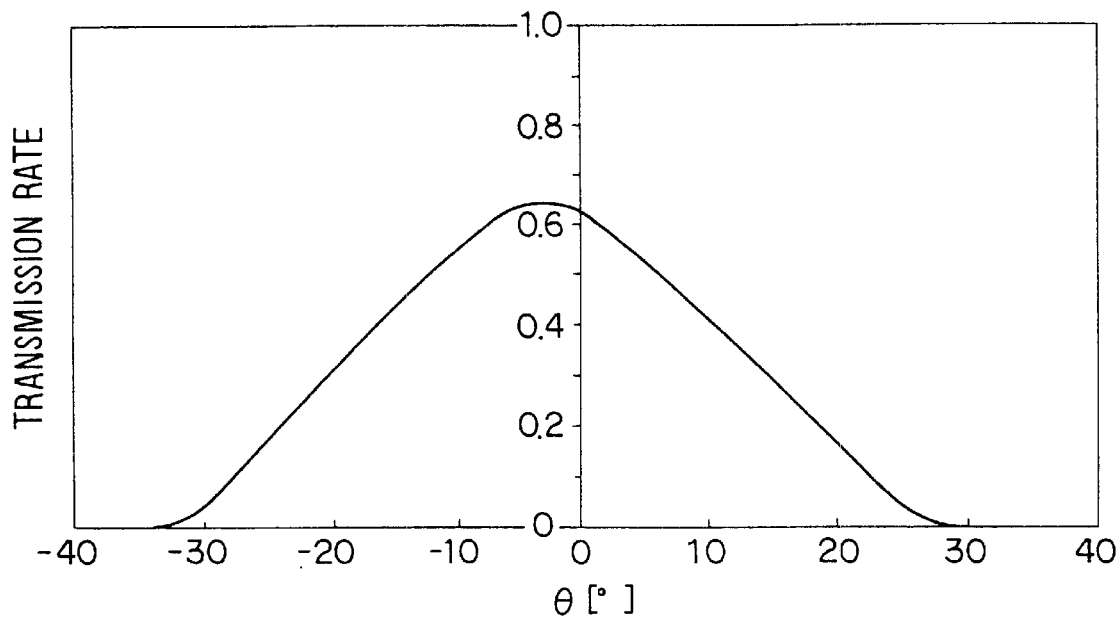
FIG. 19 is a characteristic chart of a light control film.
Figure 20:
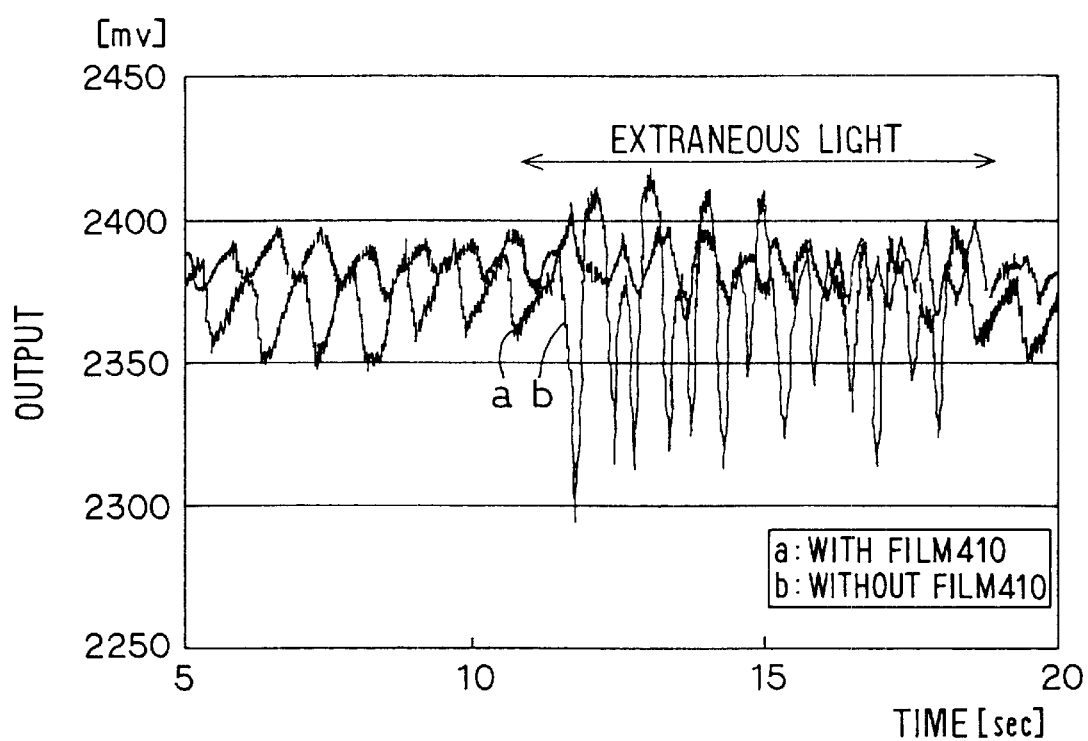
FIG. 20 is a graph showing the effect of a light control film.

Extraneous light guided in through the skin of the finger F can be considered to enter the light-receiving device 404 at a large angle of incidence. The reason for this is that when a film having the characteristic shown in FIG. 19 (not transmitting light with an angle of incidence greater than 35°) was provided above the light-receiving device 404 and its influence investigated, the influence of extraneous light fluctuations decreased, as shown in FIG. 20. Therefore, by disposing the light control film 410 above the light-receiving device 404, because extraneous light with an angle of incidence above a predetermined value (for example 35°) can be cut out, erroneous detection caused by the influence of extraneous light can be reduced and the detection capability can be increased.

When the pulse wave sensor 401 is attached to the finger F with the fixing belt 407, because the finger F is covered with the fixing belt 407 in the circumferential direction, any extraneous light reaching the pulse wave sensor 401 is guided in the length direction of the finger F. Therefore, the light control film 410 must be given an angle dependency in the length direction of the finger F.

In the case of this preferred embodiment, the light control film 410 can also be used as the light-transmitting plate 405. For example when the light control film 410 is used superposed on the light-transmitting plate 405, because the refractive indices of the two are different, reflection occurs at the interface between the light-transmitting plate 405 and the film 410. However, if the light control film 410 is used as the light-transmitting plate 405, reflection at such an interface can be eliminated.

When the light control film 410 is used superposed on the light-transmitting plate 405, because naturally the number of parts is greater and also it becomes necessary for the refractive indices of the two to be adjusted with an adjusting liquid or the like. Even if the light control film 410 is used as the light-transmitting plate 405, on the other hand, there is no increase in the number of parts and no adjustment of refractive indices is necessary.

(Twelfth Preferred Embodiment)

Figure 21:
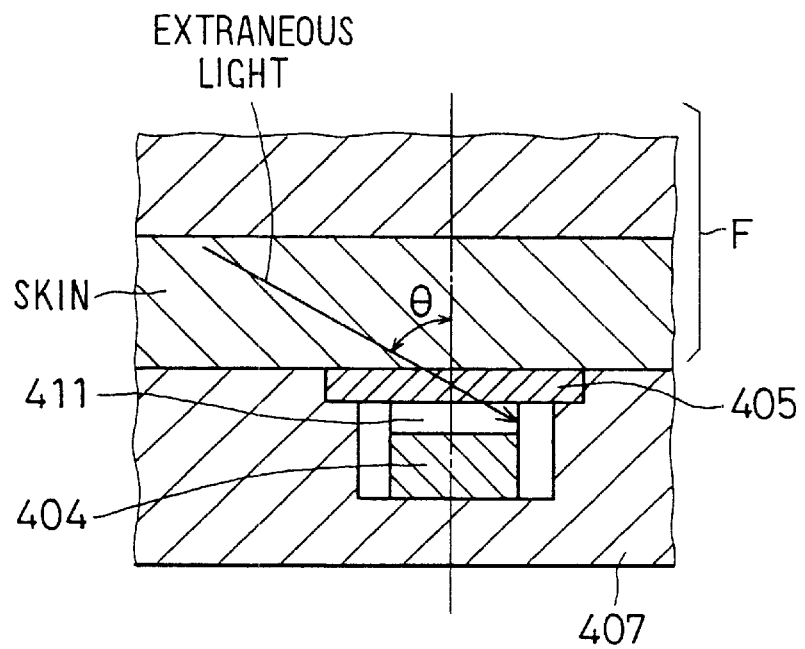
FIG. 21 is a sectional view of pulse wave sensor constituting a twelfth preferred embodiment, wherein an IR-cut filter is used.

In this embodiment, the pulse wave sensor 401 has an IR-cut filter 411 is disposed above the light-receiving device 404 as shown in FIG. 21.

When extraneous light enters the light-receiving device 404 through the finger F as a light guide, light whose wavelength is below 700 nm cannot reach the light-receiving device 404 through the finger F as a light guide. Thus, it is only necessary to block light whose wavelength is at least 700 nm. By providing the IR-cut filter 411 capable of blocking light of wavelengths greater than 700 nm above the light-receiving device 404, extraneous light entering through the finger F as a light guide can be cut out, erroneous detection caused by the influence of extraneous light can be reduced, and thus the detection probability can be increased.

In the case of this preferred embodiment, the IR-cut filter 411 can also be used as the light-transmitting plate 405. For example when the IR-cut filter 411 is used superposed on the light-transmitting plate 405, because the refractive indices of the two are different, reflection occurs at the interface between the light-transmitting plate 405 and the filter 411. However, if the IR-cut filter 411 is used as the light-transmitting plate 405, reflection at such an interface can be eliminated.

When the IR-cut filter 411 is used superposed on the light-transmitting plate 405, naturally the number of parts is greater, and also it becomes necessary for the refractive indices of the two to be adjusted with an adjusting liquid or the like. On the other hand, if the IR-cut filter 411 is used as the light-transmitting plate 405, because there is no increase in the number of parts and no adjustment of refractive indices is necessary, costs can be kept down.

(Thirteenth Preferred Embodiment)

Figure 22:
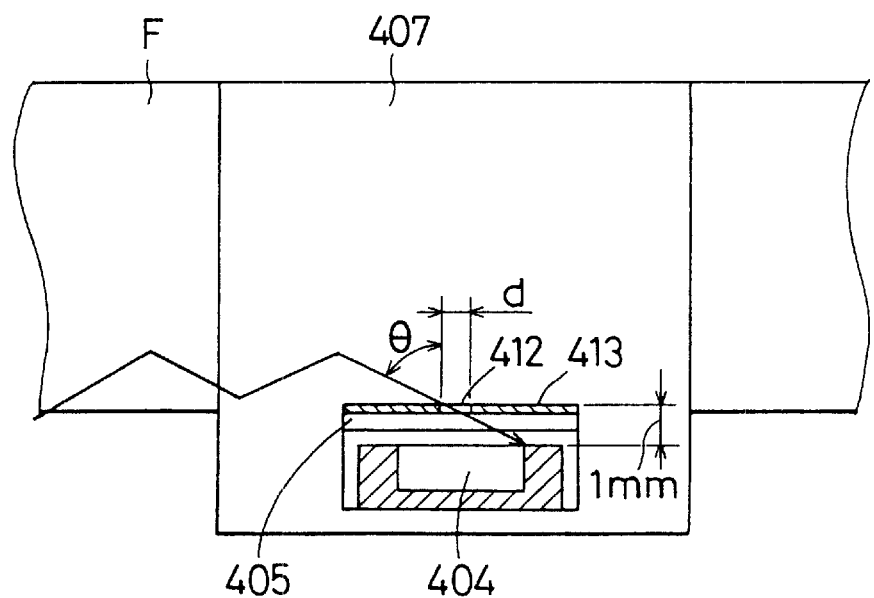
FIG. 22 is a schematic view of a thirteenth preferred embodiment, wherein a window is provided above the light-receiving device.

As shown in FIG. 22, in this preferred embodiment, a window 412 for limiting the angle of incidence at which light can enter the light-receiving device 404 is provided above the light-receiving device 404.

The window 412 above the light-receiving device 404 is formed by providing a blocking film 413 capable of blocking light on the surface of the light-transmitting plate 405 and then making a hole of a predetermined size in the center of this blocking film 413.

By providing the window 412 above the light-receiving device 404, for example as shown in FIG. 22, the light-receiving device 404 is disposed 1 mm below the interface between the light-transmitting plate 405 and the skin surface. If the window width d is made 0.5 mm, then it is possible to cut out light having an angle of incidence $\theta$ of over ±30°, as shown in FIG. 23B.

On the other hand, if the window width d is made 4 mm, then because only light whose angle of incidence $\theta$ is over ±60° is blocked, fluctuation arises in the detection result (voltage Value) of the pulse wave sensor 401 due to the influence of extraneous light, as shown in FIG. 23A.

As mentioned above with reference to the eleventh preferred embodiment, extraneous light guided in through the skin of the finger F can be considered to be incident on the light-receiving device 404 at a large angle of incidence ($\theta \geq 30°$). Consequently, since extraneous light can be effectively cut out by limiting the window width d, it is possible to reduce erroneous detection caused by the influence of extraneous light.

(Fourteenth Preferred Embodiment)

Figure 24:
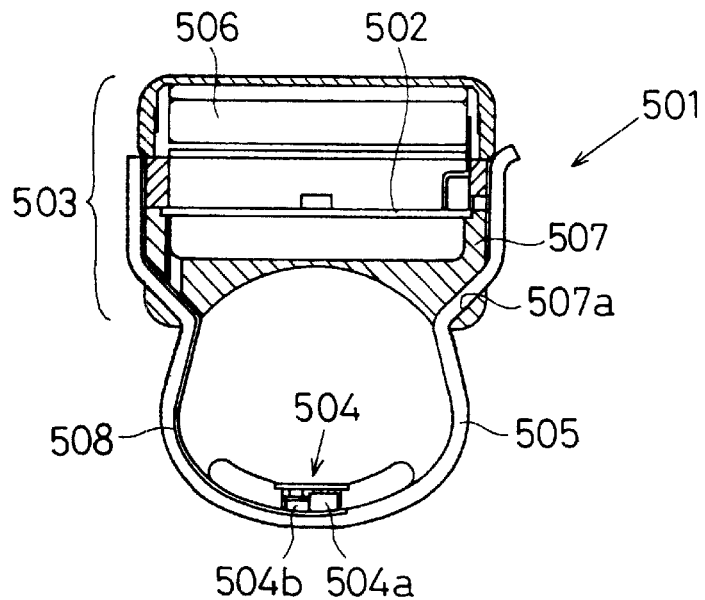
FIG. 24 is a sectional view of a pulse wave sensor constituting a fourteenth preferred embodiment of the invention.

A pulse wave sensor 501 of this preferred embodiment has, as shown in FIG. 24, the form of a finger ring for fitting to a human finger and is made up of a sensor part 503, a detecting part 504 for detecting data of the pulse wave of the body, and a belt 505 for fixing the sensor part 503 to the finger.

The sensor part 503 has a circuit part 502 and a battery 506, and is received inside a housing 507. The circuit part 502 comprises a transmitting circuit for transmitting to an outside receiver via an antenna (not shown) pulse wave data (for example, a voltage signal) sent to it through signal wires from the detecting part 504.

Figure 25:
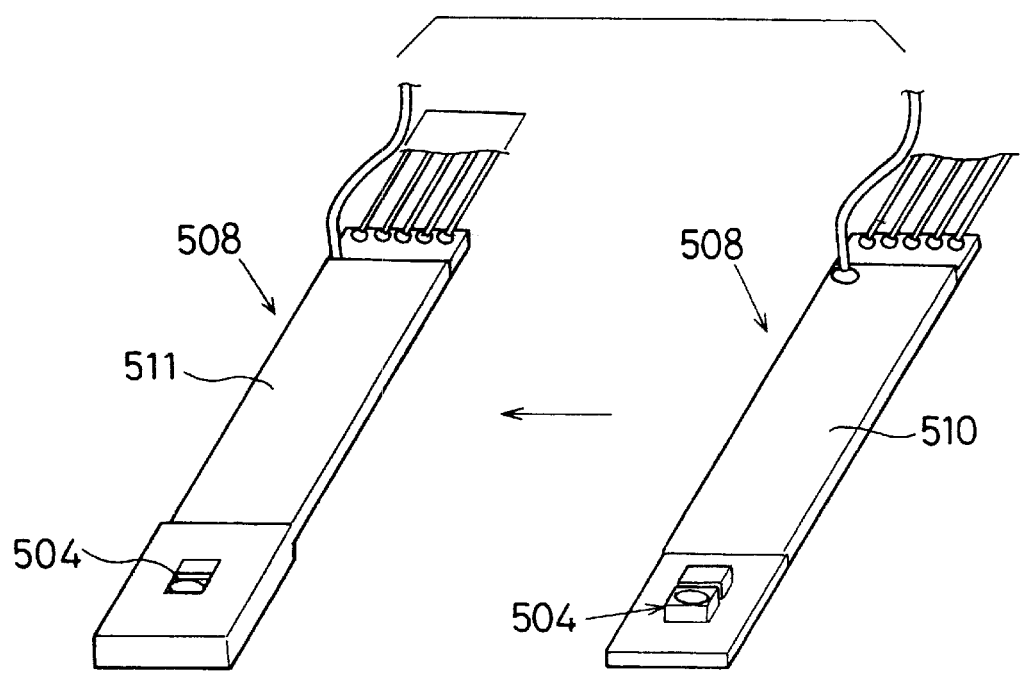
FIG. 25 is a perspective view of a printed circuit board used in the same pulse wave sensor.

The signal wires connecting the circuit part 502 with the detecting part 504 are printed as an interconnection pattern on a printed circuit board 508 as shown in FIG. 25. This printed circuit board 508 has one end connected inside the housing 507 to the circuit part 502 and extends to outside the housing 507 through a hole 507a provided in the housing 507 for the belt 505 to pass through.

The detecting part 504 is an ordinary reflection-type sensor comprising a light-emitting device 504a and a light-receiving device 504b disposed side by side and is mounted on the end of the printed circuit board 508 extending to outside the housing 507 and projects several millimeters (for example, 2 to 5 mm) from the surface of the printed circuit board 508, as shown in FIG. 25.

Figure 26:
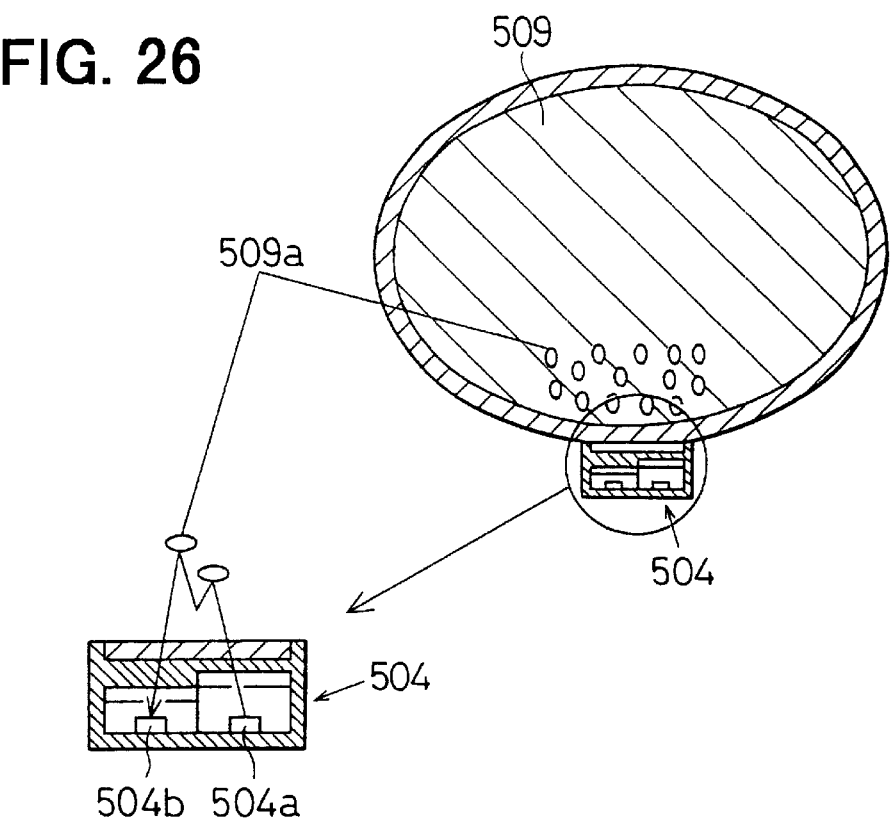
FIG. 26 is a sectional view of a detecting part of the same pulse wave sensor fitted to a finger.

When light is emitted from the light-emitting device 504a toward the finger 509, as shown in FIG. 26, some of the light strikes blood capillaries 509a passing through the inside of the finger 509 and is absorbed by haemoglobin in blood flowing through the blood capillaries 509a. The rest of the light is reflected and scattered by the blood capillaries 509a, and some of this enters the light-receiving device 504b. At this time, because the amount of haemoglobin in the blood capillaries 509a varies in a wave pattern due to pulsation of the blood, the amount of light absorbed by the haemoglobin also varies in a wave pattern. As a result, the light reflected by the blood capillaries 509a and entering the light-receiving device 504b also varies, and this variation in the amount of received light is detected as pulse wave data.

The printed circuit board 508 is constructed with for example a flexible polyimide thermoplastic resin as a base material. It flexibly links the sensor part 503 and the detecting part 504 and is provided in a shape curved in advance to follow the circumference of a finger.

Also, as shown in FIG. 25, the entire printed circuit board 508 is shielded by being covered with a conductor such as a copper foil 510 electrically connected to a ground of the circuit part 502 and the surface of the copper foil 510 being insulated by an insulating tape 511 or the like. Of course, the detection face of the detecting part 504 is exposed.

The belt 505 covers the outer side of the printed circuit board 508 and is attached to the housing 507 of the sensor part 503 and can be fastened with magic tape or the like so that its length can be adjusted with respect to the sensor part 503. The material of the belt 505 is preferably a material that will conform to the finger, such as cloth, leather, a stretchable material (knit), rubber, or a soft resin (for example urethane, elastomer, polyester elastomer). When cloth, leather or knit is used as the material of the belt 505, it may be waterproofed to prevent the absorption of water into the belt 505 during hand-washing and work involving water and so on.

In using this pulse wave sensor 501, the sensor part 503 is disposed on the rear side of the finger so that the detecting part 504 faces the belly side of the finger, and the sensor part 503 is fixed with the belt 505. At this time, the length of the belt 505 is adjusted so that the detecting part 504 makes close contact with the belly of the finger, so that the detecting part 504 is pressed against the belly of the finger.

In the pulse wave sensor 501 of this preferred embodiment, because the sensor part 503 and the detecting part 504 are connected flexibly by the flexible printed circuit board 508, movement of the sensor part 503 is not readily transmitted to the detecting part 504, and slipping of the detecting part 504 along with movement of the body can be suppressed. Thus, a pulse wave sensor 501 which is tolerant of movement can be realized.

Because the sensor part 503 is fixed to the finger with the belt 505, by adjusting the length of the belt 505 it is possible to fix the sensor part 503 to the finger with the detecting part 504 pressed against the surface of the finger. Consequently, since the pulse wave sensor 501 can be used with the detecting part 504 in close contact with the finger at all times, irrespective of the size of the finger, the influence of extraneous light can be reduced and an accurate pulse wave can be detected.

Although the sensor part 503 and the detecting part 504 are connected by the printed circuit board 508, by the printed circuit board 508 being given a shielded structure it is possible to prevent the ingress of noise (for example from a commercial power supply) from the signal wires to the circuit part 502, and consequently a highly accurate pulse wave can be measured.

In the preferred embodiment described above, an antenna is provided in the circuit part 502 to transmit pulse wave data from the circuit part 502 to an outside receiver. However, this antenna may alternatively be inserted in the belt 505. As the method for fastening the belt 505, besides magic tape, any of various metal fastenings may alternatively be used.

(Fifteenth Preferred Embodiment)

Figure 27:
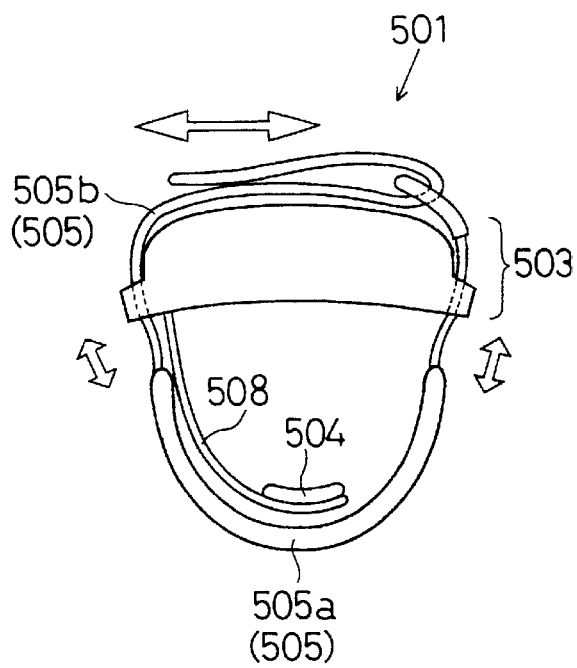
FIG. 27 is a side view of a pulse wave sensor constituting a fifteenth preferred embodiment of the invention.

The pulse wave sensor 501 of this preferred embodiment differs from the fourteenth preferred embodiment in the structure by which the sensor part 503 is attached to the belt 505. Here, as shown in FIG. 27, the belt 505 is fastened by magic tape or the like above the sensor part 503 (on the top side in FIG. 27).

Also, in the belt 505, a material which conforms to the finger may be used for the part 505a contacting the belly side of the finger, and an expandable material used for the part 505b attached to the sensor part 503.

(Sixteenth Preferred Embodiment)

Figure 28A:
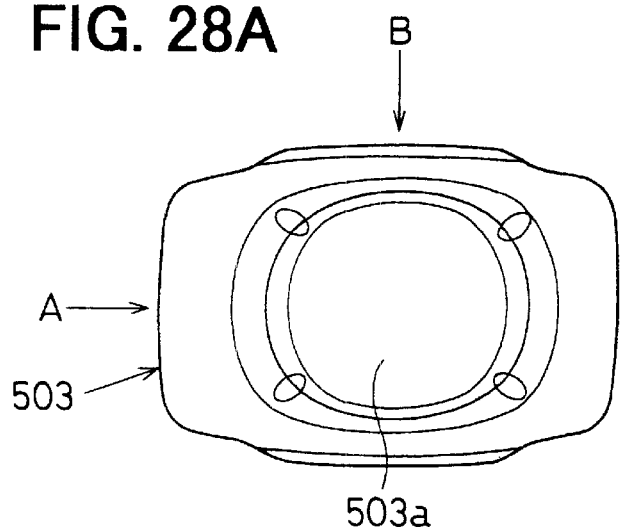
FIGS. 28A through 28C are three elevations of a pulse wave sensor constituting a sixteenth preferred embodiment of the invention.
Figure 28B:
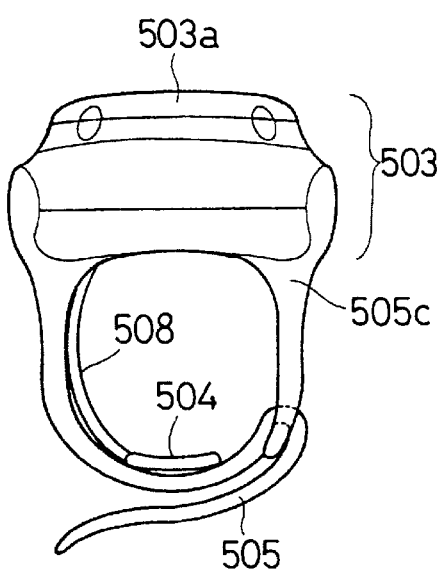
Figure 28C:
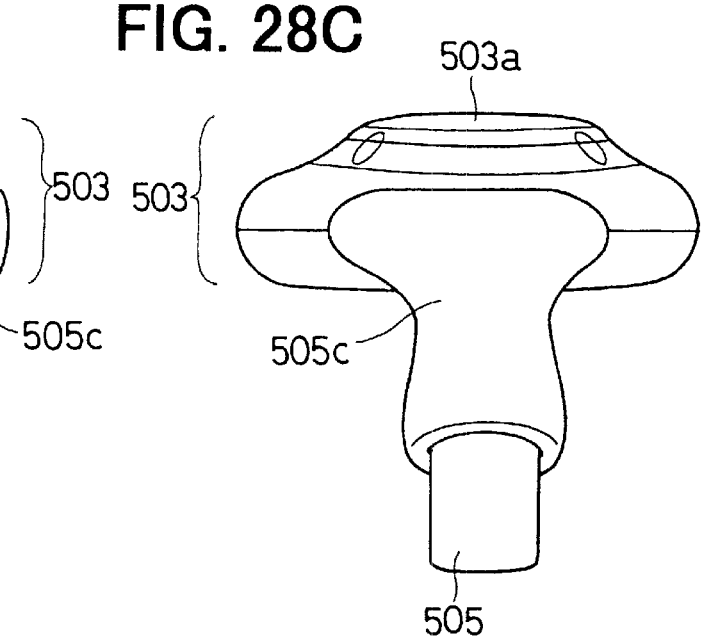

In the pulse wave sensor 501 of this preferred embodiment, as shown in FIGS. 28A through 28C, end parts 505c of the belt 505 fixed to the sensor part 503 are made thick or relatively hard. In this case, because the force with which the device is held on the finger can be increased, a pulse wave sensor 501 tolerant of movement of the body can be realized. Also, a display part 503a capable of displaying pulse wave data may be provided on the top face of the sensor part 503.

(Seventeenth Preferred Embodiment)

Figure 29:
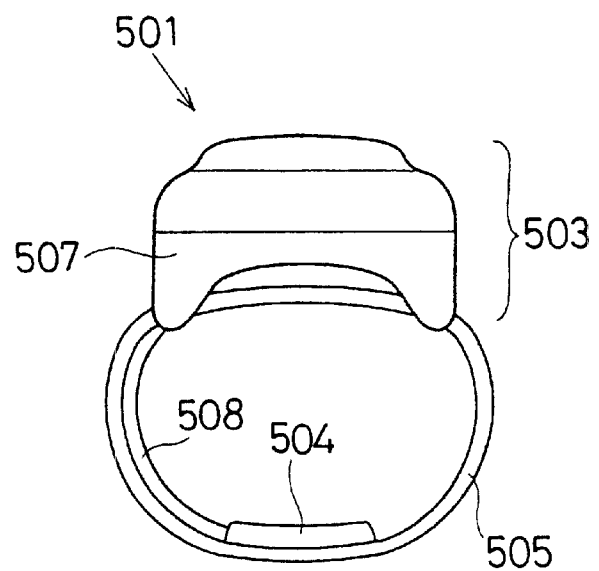
FIG. 29 is a side view of a pulse wave sensor constituting a seventeenth preferred embodiment of the invention.

The pulse wave sensor 501 of this preferred embodiment, as shown in FIG. 29, has a construction wherein the belt 505 is passed through holes provided in the housing 507 of the sensor part 503 and forms the shape of a ring and can be freely moved with respect to the housing 507. In this case, because there is almost no transmission of movement of the housing 507 through the belt 505 to the detecting part 504, a pulse wave sensor 501 more tolerant of movement can be realized.

(Eighteenth Preferred Embodiment)

Figure 30:
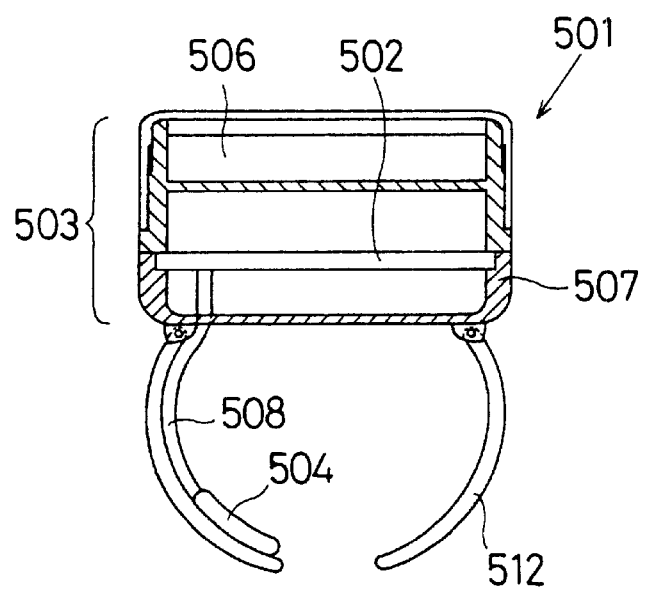
FIG. 30 is a side view of a pulse wave sensor constituting an eighteenth preferred embodiment of the invention.

In the pulse wave sensor 501 of this preferred embodiment, as shown in FIG. 30, parts for fixing the sensor part 503 to the finger are provided in the form of a clip, and the pulse wave sensor 501 is used with these clip-like fixing parts 512 gripping the finger from opposite sides. In this case, by the clip-like fixing parts 512 being given elasticity, the sensor part 503 can be fixed stably to the finger irrespective of the size (thickness) of the finger.

The present invention should not be limited to the disclosed embodiments, but may be implemented in many other ways without departing from the spirit of the invention.

What is claimed is:

1. A vital signal detecting apparatus, comprising:
an attachable device to be attached to a human body;
vital signal detecting means, disposed on the attachable device on a side thereof to be attached to the body, for detecting a vital signal of the body the vital signal detecting means including a light-emitting device for emitting light through skin into the body and a light-receiving device for receiving light returning from inside the body and outputting a signal corresponding to the amount of light received;

attachment state detecting means for detecting a state of attachment/detachment of the attachable device to the body for detecting the state of attachment/detachment of the attachable device to the body on the basis of a signal outputted by the light-receiving device when the light-emitting device is on and a signal outputted by the light-receiving device when the light-emitting device is off; and processing alteration means for, on the basis of a detection result of the attachment state detecting means, altering detection processing for detecting the vital signal of the body.

2. The vital signal detecting apparatus of claim 1, wherein:

the attachment state detecting mean compares the signal outputted by the light-receiving device when the light-emitting device is on with the signal outputted by the light-receiving device when the light-emitting device is off and detects that the attachable device is detached when the two signals are of substantially the same level and detects that the attachable device is attached when there is a difference in level between the two signals.

3. The vital signal detecting apparatus of claim 1, wherein:

the attachment state detecting means detects the state of attachment/detachment of the attachable device to the body by comparing a d.c. component of the signal outputted by the light-receiving device when the light-emitting device is on with a d.c. component of the signal outputted by the light-receiving device when the light-emitting device is off.

4. A vital signal detecting apparatus of claim 1, wherein:

the processing alteration means stops the detection of the vital signal effected by the vital signal detecting means, when the attachment state detecting means detects that the attachable device is detached from the body.

5. A vital signal detecting apparatus of claim 4, wherein:

the processing alteration means restarts the detection of the vital signal or restarts a supply of operating power when a predetermined time has elapsed from a stopping of the detection of the vital signal effected by the vital signal detecting means or a stopping of a supply of operating power to the vital signal detecting means.

6. A vital signal detecting apparatus of claim 1, wherein:

the processing alteration means stops a supply of operating power to the vital signal detecting means when the attachment state detecting means detects that the attachable device is detached from the body.

7. A vital signal detecting apparatus of claim 1, further comprising:

a vital signal processing unit to which the vital signal is transmitted and which computes a parameter manifesting a state of the body on the basis of this vital signal, wherein data relating to the state of attachment/detachment of the attachable device to the body is also transmitted to the vital signal processing unit and, while it is detected that the attachable device is not attached to the body, the processing alteration means stops the computing of the parameter based on the vital signal in the vital signal processing unit.

8. A vital signal detecting apparatus of claim 7, wherein:

the vital signal processing unit comprises reporting means for reporting to that effect, when data indicating a state of detachment of the attachable device to the body is transmitted to the vital signal processing unit.

9. A vital signal detecting apparatus of claim 1, wherein:

the attachment state detecting means includes a pushable part to be pushed by the body as the attachable device is attached to the body, and a detecting part for detecting whether or not the pushable part is being pushed.

10. A vital signal detecting apparatus of claim 1, wherein:

the attachment state detecting means has a temperature-sensitive device which responds to the body temperature when the attachable device is attached to the body.

11. A vital signal detecting apparatus of claim 1, wherein:

the attachment state detecting means has an electric circuit which incorporates the body as a part of the circuit when the attachable device is attached to the body; and the attachment state detecting means detects attachment of the attachable device to the body by detecting a change in a resistor, a static capacitance or a potential occurring when the attachable device is attached to the body.

12. A vital signal detecting apparatus comprising:

a light-emitting device;

a light-receiving device; and a light-transmitting plate disposed above the light-emitting device and the light-receiving device to pass light therethrough, and used with the surface of the light-transmitting plate in contrast with the skin surface of a human body, wherein the light-receiving device is disposed in a position lowered by a predetermined distance with respect to the light-transmitting plate, and wherein the light-emitting device is disposed closer than the light-receiving device to the light-transmitting plate.

13. A vital signal detecting apparatus comprising:

a light-emitting device;

a light-receiving device; and a light-transmitting plate disposed above the light-emitting device and the light-receiving device to pass light therethrough, and used with the surface of the light-transmitting plate in contrast with the skin surface of a human body, wherein the light-receiving device is disposed in a position lowered by a predetermined distance with respect to the light-transmitting plate, and a window formed in a light-blocking layer that covers the surface of the light-transmitting plate and provided above the light-receiving device, the window for limiting the angle of incidence at which light can enter the light-receiving device.

* * * * *